US011135026B2

United States Patent
Bono et al.

(10) Patent No.: US 11,135,026 B2
(45) Date of Patent: Oct. 5, 2021

(54) ROBOTIC SURGICAL SYSTEM

(71) Applicant: Peter L. Bono, Bingham Farms, MI (US)

(72) Inventors: Peter L. Bono, Bingham Farms, MI (US); James D. Lark, West Bloomfield, MI (US); John S. Scales, Ann Arbor, MI (US); Thomas J. Lord, South Milwaukee, WI (US)

(73) Assignee: Peter L. Bono, Bingham Farms, MI (US)

( * ) Notice: Subject to any disclaimer, the term of this patent is extended or adjusted under 35 U.S.C. 154(b) by 528 days.

(21) Appl. No.: 15/816,861

(22) Filed: Nov. 17, 2017

(65) Prior Publication Data

US 2018/0168757 A1 Jun. 21, 2018

Related U.S. Application Data

(63) Continuation-in-part of application No. 13/469,665, filed on May 11, 2012, now Pat. No. 10,194,922, and
(Continued)

(51) Int. Cl.
*A61B 34/35* (2016.01)
*A61B 34/00* (2016.01)
(Continued)

(52) U.S. Cl.
CPC ........ *A61B 34/35* (2016.02); *A61B 17/32002* (2013.01); *A61B 34/25* (2016.02);
(Continued)

(58) Field of Classification Search
CPC ......... A61B 34/25; A61B 34/35; A61B 34/76; A61B 2034/252; A61B 2090/3925; A61B 2090/3966
See application file for complete search history.

(56) References Cited

U.S. PATENT DOCUMENTS

| 1,154,159 A | 9/1915 | Ashworth |
| 2,557,429 A | 6/1951 | Hawley |
| (Continued) | | |

FOREIGN PATENT DOCUMENTS

| AR | 42807 | 7/2005 |
| AT | 370608 | 4/1983 |
| (Continued) | | |

OTHER PUBLICATIONS

MasterCut Tool Corp., Bur Series, Metric, (2018).
(Continued)

*Primary Examiner* — Anu Ramana
(74) *Attorney, Agent, or Firm* — McHale & Slavin, P.A.

(57) ABSTRACT

The present invention provides an apparatus, system and method for providing robotically assisted surgery that involves the removal of bone or non-fibrous type tissues during a surgical procedure. The system utilizes a multi-axis robot having a reciprocating tool that is constructed and arranged to remove hard or non-fibrous tissues while leaving soft tissues unharmed. The multi-axis robot may be controlled via computer or telemanipulator, which allows the surgeon to complete a surgery from an area adjacent to the patient to thousands of miles away.

10 Claims, 22 Drawing Sheets

Related U.S. Application Data a continuation-in-part of application No. 15/814,891, filed on Nov. 16, 2017, now Pat. No. 10,835,263.

(60) Provisional application No. 62/423,677, filed on Nov. 17, 2016, provisional application No. 62/423,651, filed on Nov. 17, 2016, provisional application No. 62/423,624, filed on Nov. 17, 2016.

(51) Int. Cl.
*A61B 17/32* (2006.01)
*A61B 34/30* (2016.01)
*A61B 17/00* (2006.01)
*A61B 90/00* (2016.01)

(52) U.S. Cl.
CPC .............. *A61B 34/30* (2016.02); *A61B 34/76* (2016.02); *A61B 34/74* (2016.02); *A61B 2017/00477* (2013.01); *A61B 2017/320028* (2013.01); *A61B 2034/305* (2016.02); *A61B 2090/378* (2016.02); *A61B 2090/3925* (2016.02); *A61B 2090/3966* (2016.02)

(56) References Cited

U.S. PATENT DOCUMENTS

| | | | |
|---|---|---|---|
| 2,831,295 A | 4/1958 | Weiss | |
| 3,091,060 A | 5/1963 | Giegerich et al. | |
| 3,554,197 A | 1/1971 | Dobbie | |
| 3,577,579 A | 5/1971 | Duve | |
| 4,007,528 A | 2/1977 | Shea et al. | |
| 4,008,720 A | 2/1977 | Brinckmann et al. | |
| 4,081,704 A | 3/1978 | Vassos et al. | |
| RE29,736 E | 8/1978 | Shea et al. | |
| D248,967 S | 8/1978 | Shea et al. | |
| 4,111,208 A | 9/1978 | Leuenberger | |
| 4,596,243 A | 6/1986 | Bray | |
| 4,620,539 A | 11/1986 | Andrews et al. | |
| 4,828,052 A | 5/1989 | Duran et al. | |
| 4,932,935 A | 6/1990 | Swartz | |
| 5,092,875 A | 3/1992 | McLees | |
| 5,522,829 A | 6/1996 | Michalos | |
| 5,733,119 A | 3/1998 | Carr | |
| 5,843,110 A | 12/1998 | Dross et al. | |
| 6,021,538 A | 2/2000 | Kressner et al. | |
| 6,110,174 A | 8/2000 | Nichter | |
| 6,546,279 B1 | 4/2003 | Bova et al. | |
| 6,606,539 B2* | 8/2003 | Raab .............. | B25J 9/1692 33/503 |
| 6,635,067 B2 | 10/2003 | Norman | |
| 6,689,087 B2 | 2/2004 | Pal et al. | |
| 6,716,215 B1 | 4/2004 | David et al. | |
| 6,721,986 B2 | 4/2004 | Zhuan | |
| 6,895,305 B2* | 5/2005 | Lathan .............. | A63F 13/00 700/245 |
| 6,966,912 B2 | 11/2005 | Michelson | |
| 7,160,304 B2 | 1/2007 | Michelson | |
| 7,194,120 B2 | 3/2007 | Wicker et al. | |
| 7,346,417 B2 | 3/2008 | Luth et al. | |
| 7,660,623 B2* | 2/2010 | Hunter .............. | A61F 2/4657 600/424 |
| 7,922,720 B2 | 4/2011 | May et al. | |
| 8,029,523 B2 | 10/2011 | Wallis et al. | |
| 8,038,630 B2 | 10/2011 | Pal et al. | |
| 8,170,717 B2 | 5/2012 | Sutherland et al. | |
| 8,219,178 B2 | 7/2012 | Smith et al. | |
| 8,465,491 B2 | 6/2013 | Yedlicka et al. | |
| 8,491,603 B2 | 7/2013 | Yeung et al. | |
| 8,657,821 B2 | 2/2014 | Palermo | |
| 8,728,085 B2 | 5/2014 | Marsh et al. | |
| 8,828,001 B2 | 9/2014 | Stearns et al. | |
| 8,943,634 B2 | 2/2015 | Sokol et al. | |
| 2001/0015649 A1 | 8/2001 | Herrmann et al. | |
| 2003/0060927 A1 | 3/2003 | Gerbi et al. | |

| | | | |
|---|---|---|---|
| 2004/0050603 A1 | 3/2004 | Jaeger | |
| 2004/0147934 A1 | 7/2004 | Kiester | |
| 2005/0027397 A1 | 2/2005 | Niemeyer | |
| 2005/0043718 A1 | 2/2005 | Madhani et al. | |
| 2005/0171557 A1 | 8/2005 | Shoham | |
| 2005/0283175 A1 | 12/2005 | Tanner et al. | |
| 2006/0229624 A1 | 10/2006 | May et al. | |
| 2006/0235305 A1 | 10/2006 | Cotter et al. | |
| 2006/0235306 A1 | 10/2006 | Cotter et al. | |
| 2007/0005045 A1* | 1/2007 | Mintz .............. | A61B 34/74 606/1 |
| 2007/0021738 A1 | 1/2007 | Hasser et al. | |
| 2007/0276423 A1 | 11/2007 | Green | |
| 2007/0282344 A1 | 12/2007 | Yedlicka et al. | |
| 2007/0282345 A1 | 12/2007 | Yedlicka et al. | |
| 2008/0027449 A1 | 1/2008 | Gundlapalli et al. | |
| 2008/0061784 A1 | 3/2008 | Pal et al. | |
| 2008/0108010 A1 | 5/2008 | Wang | |
| 2008/0108991 A1 | 5/2008 | von Jako | |
| 2008/0213889 A1 | 9/2008 | Olgac | |
| 2010/0145343 A1 | 6/2010 | Johnson et al. | |
| 2010/0165793 A1 | 7/2010 | Haug | |
| 2010/0198230 A1 | 8/2010 | Shoham | |
| 2010/0249506 A1 | 9/2010 | Prisco | |
| 2010/0249786 A1 | 9/2010 | Schmieding et al. | |
| 2011/0015635 A1 | 1/2011 | Aryan | |
| 2011/0118708 A1 | 5/2011 | Burbank et al. | |
| 2011/0118709 A1 | 5/2011 | Burbank | |
| 2011/0118778 A1 | 5/2011 | Burbank | |
| 2011/0196404 A1 | 8/2011 | Dietz et al. | |
| 2011/0230886 A1 | 9/2011 | Gustilo et al. | |
| 2011/0295270 A1 | 12/2011 | Giordano et al. | |
| 2011/0306873 A1 | 12/2011 | Shenai et al. | |
| 2011/0313428 A1 | 12/2011 | Mohr et al. | |
| 2011/0319941 A1 | 12/2011 | Bar et al. | |
| 2012/0059392 A1 | 3/2012 | Diolaiti | |
| 2012/0186372 A1 | 7/2012 | Smith et al. | |
| 2012/0211546 A1 | 8/2012 | Shelton, IV | |
| 2012/0220831 A1 | 8/2012 | Cooper et al. | |
| 2012/0266442 A1 | 10/2012 | Rogers et al. | |
| 2013/0096540 A1 | 4/2013 | Cooper et al. | |
| 2013/0123799 A1 | 5/2013 | Smith et al. | |
| 2013/0178856 A1 | 7/2013 | Ye et al. | |
| 2013/0206441 A1 | 8/2013 | Roser et al. | |
| 2013/0244820 A1 | 9/2013 | Solomon et al. | |
| 2013/0245629 A1 | 9/2013 | Xie | |
| 2013/0296886 A1 | 11/2013 | Green et al. | |
| 2013/0304069 A1 | 11/2013 | Bono et al. | |
| 2013/0345718 A1 | 12/2013 | Crawford et al. | |
| 2014/0051922 A1 | 2/2014 | Guthart et al. | |
| 2014/0100574 A1 | 4/2014 | Bono et al. | |
| 2014/0194894 A1 | 7/2014 | Dachs, II et al. | |
| 2014/0222003 A1 | 8/2014 | Herndon et al. | |
| 2014/0350391 A1 | 11/2014 | Prisco et al. | |
| 2015/0119916 A1 | 4/2015 | Dietz et al. | |
| 2016/0151120 A1 | 6/2016 | Kostrzewski et al. | |

FOREIGN PATENT DOCUMENTS

| | | |
|---|---|---|
| AU | 2011215901 | 1/2003 |
| AU | 2003200831 | 8/2004 |
| BE | 861446 | 3/1978 |
| CA | 1112970 | 11/1981 |
| CA | 2513071 | 7/2004 |
| CA | 2788918 | 8/2011 |
| CH | 610753 | 5/1979 |
| CL | 252004 | 3/2005 |
| CN | 102781349 | 11/2012 |
| DE | 2730227 | 12/1980 |
| DK | 570977 | 6/1978 |
| EP | 0148304 | 7/1985 |
| EP | 0261260 | 3/1988 |
| EP | 1571581 | 3/2005 |
| EP | 1041918 | 3/2006 |
| EP | 1581374 | 8/2006 |
| EP | 1690649 | 8/2006 |
| EP | 2533703 | 12/2012 |
| ES | 465719 | 12/1980 |
| FI | 773650 | 6/1978 |

(56) References Cited

FOREIGN PATENT DOCUMENTS

| | | |
|---|---|---|
| FR | 2374886 | 7/1978 |
| GB | 1550577 | 8/1979 |
| IT | 1081824 | 5/1985 |
| JP | 2006512954 | 4/2006 |
| JP | 4481173 | 6/2010 |
| JP | 2013519434 | 5/2013 |
| JP | S5380789 | 1/2014 |
| JP | S5613462 | 10/2014 |
| JP | 5826771 | 12/2015 |
| NL | 7713563 | 6/1978 |
| NO | 774411 | 6/1978 |
| WO | WO9107116 | 5/1991 |
| WO | WO0215799 | 2/2002 |
| WO | WO2004062863 | 7/2004 |
| WO | WO2007008703 | 1/2007 |
| WO | WO2009151926 | 12/2009 |
| WO | WO2011100313 | 8/2011 |
| WO | WO20122166476 | 12/2012 |
| WO | WO2014150514 | 9/2014 |
| WO | WO2015006296 | 1/2015 |
| WO | WO2015166487 | 11/2015 |

OTHER PUBLICATIONS

MasterCut Tool Corp., Bur Series, US, (2010).
News & Notes, British Dental Journal, vol. 191, No. 7, pp. 410-411 (Oct. 13, 2001).
Tungsten Carbide Drills Mills & Burs, Internet catalogue, http://chinatungsten.com/picture-bank/tungsten-carbide-drills.html, (Retrieved Feb. 7, 2018).
Cutting Tool, Drill Bit, End Mill, Internet catalogue, http://lzqtool.com/include/search.aspx?keycode=c-grade&type=1&language=en, (Retrieved Feb. 7, 2018).

\* cited by examiner

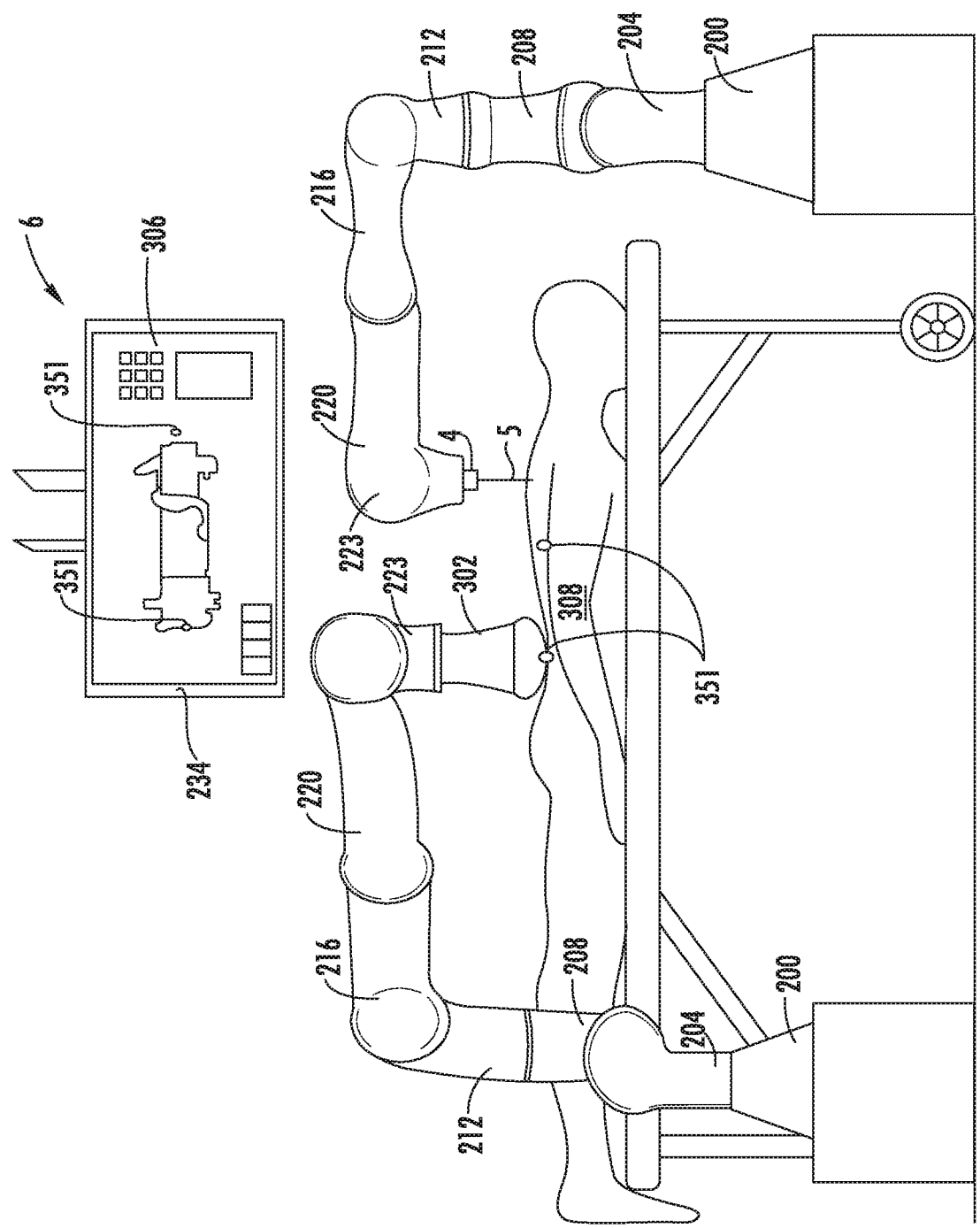

ROBOTIC SURGICAL SYSTEM

CROSS REFERENCE TO RELATED APPLICATIONS

In accordance with 37 C.F.R. 1.76, a claim of priority is included in an Application Data Sheet filed concurrently herewith. Accordingly, the present invention claims priority to U.S. Provisional Patent Application 62/423,677, filed Nov. 17, 2016, entitled "ROBOTIC SURGICAL SYSTEM", and to U.S. Provisional Patent Application No. 62/423,651, filed Nov. 17, 2016, entitled "ROBOTIC SURICAL SYSTEM". The present invention claims priority as a continuation-in-part of U.S. patent application Ser. No. 13/469,665, filed May 11, 2012, entitled "ROTARY OSCILLATING BONE, CARTILAGE, AND DISK REMOVAL TOOL ASSEMBLY", and as a continuation-in-part to U.S. patent application Ser. No. 15/814,891, filed Nov. 16, 2017, entitled "ROTARY OSCILLATING SURGICAL TOOL", which claims priority to U.S. Provisional Patent Application No. 62/423,624, filed Nov. 17, 2016, entitled "ROTARY OSCILLATING SURGICAL TOOL". The contents of each of the above referenced applications are herein incorporated by reference in its entirety.

FIELD OF THE INVENTION

The present invention relates to surgical systems and, more particularly, to a multi-axis robotic device having an end effector constructed to remove bone and non-fibrous tissues while minimizing damage to soft tissue.

BACKGROUND OF THE INVENTION

The central nervous system is a vital part of the human physiology that coordinates human activity. It is primarily made up of the brain and the spinal cord. The spinal cord is made up of a bundle of nerve tissue which originates in the brain and branches out to various parts of the body, acting as a conduit to communicate neuronal signals from the brain to the rest of the body, including motor control and sensations. Protecting the spinal cord is the spinal, or vertebral, column. Anatomically, the spinal column is made up of several regions including the cervical, thoracic, lumbar and sacral regions. The cervical spine is made up of seven vertebrae and functions to support the weight of the head. The thoracic spine is made up of twelve vertebrae and functions to protect the organs located within the chest. Five vertebrae make up the lumbar spine. The lumbar spine contains the largest vertebra and functions as the main weight bearing portion of the spine. Located at the base of the spine is the five fused vertebrae known as the sacrum. The coccyx sits at the base of the spinal column and consists of four fused vertebrae.

Each of the vertebrae associated with the various spinal cord regions are made up of a vertebral body, a posterior arch, and transverse processes. The vertebral body, often described as having a drum-like shape, is designed to bear weight and withstand compression or loading. In between the vertebral bodies is the intervertebral disc. The intervertebral disc is filled with a soft, gelatinous-like substance which helps cushion the spine against various movements and can be the source of various diseases. The posterior arch of the vertebrae is made up of the lamina, pedicles and facet joints. Transverse processes extend outwardly from the vertebrae and provide the means for muscle and ligament attachment, which aid in movement and stabilization of the vertebra.

While most people have fully functional spinal cords, it is not uncommon for individuals to suffer some type of spinal ailment, including spondylolisthesis, scoliosis, or spinal fractures. One of the more common disorders associated with the spinal cord is damage to the spinal discs. Damage to the discs results from physical injury, disease, genetic disposition, or as part of the natural aging process. Disc damage often results in intervertebral spacing not being maintained, causing pinching of exiting nerve roots between the discs, resulting in pain. For example, disc herniation is a condition in which the disc substance bulges from the disc space between the two vertebrae bodies. It is the bulging of the disc material which causes impingement on the nerves, manifesting in pain to the patient. For most patients, rest and administration of pain and anti-inflammatory medications alleviates the problem. However, in severe cases, cases which have developed into spinal instability or severe disc degeneration, the damaged disc material between the vertebral bodies is removed and replaced with spinal stabilization implants. Restoration to the normal height allows the pressure on the nerve roots to be relieved.

There are many different approaches taken to alleviate or minimize severe spinal disorders. One surgical procedure commonly used is a spinal fusion technique. Several surgical approaches have been developed over the years, and include the Posterior Lumbar Interbody Fusion (PLIF) procedure which utilizes a posterior approach to access the patient's vertebrae or disc space, the Transforaminal Lumbar Interbody Fusion (TLIF) procedure which utilizes a posterior and lateral approach to access the patient's vertebrae or disc space, and the Anterior Lumbar Interbody Fusion (ALIF) which utilizes an anterior approach to access the patient's vertebrae or disc space. Using any of these surgical procedures, the patient undergoes spinal fusion surgery in which two or more vertebrae are linked or fused together through the use of a bone spacing device and/or use of bone grafts. The resulting surgery eliminates any movement between the spinal sections which have been fused together.

In addition to the spinal implants or use of bone grafts, spinal fusion surgery often utilizes spinal instrumentation or surgical hardware, such as pedicle screws, plates, or spinal rods. Once the spinal spacers and/or bone grafts have been inserted, a surgeon places the pedicle screws into a portion of the spinal vertebrae and attaches either rods or plates to the screws as a means for stabilization while the bones fuse. Currently available systems for inserting the rods into pedicle screws can be difficult to use, particularly in light of the fact that surgeons installing these rods often work in narrow surgical fields. Moreover, since patients can vary with respect to their internal anatomy, resulting in varying curvatures of the spine, a surgeon may not always have a linear path or may have anatomical structures that must be maneuvered around in order to properly insert the surgical rods into the pedicle screw assemblies. In addition to requiring surgical skill, difficulty in placing the rods correctly into the pedicle screws can result in unnecessary increases in the time it takes a surgeon to complete the surgical procedure. Prolonged surgery times increase the risk to the patient. More importantly, improperly aligning the rods and pedicle screw assemblies often results in post-surgery complications for the patient and requires corrective surgical procedures.

Robotic surgery, computer-assisted surgery, and robotically-assisted surgery are terms for technological developments that use robotic systems to aid in surgical procedures.

Robotically-assisted surgery was developed to overcome the limitations of pre-existing minimally-invasive surgical procedures and to enhance the capabilities of surgeons performing open surgery.

In the case of robotically-assisted minimally-invasive surgery, instead of directly moving the instruments, the surgeon uses one of two methods to control the instruments; either a direct telemanipulator or through computer control. A telemanipulator is a remote manipulator that allows the surgeon to perform the normal movements associated with the surgery while the robotic arms carry out those movements using end-effectors and manipulators to perform the actual surgery on the patient. In computer-controlled systems, the surgeon uses a computer to control the robotic arms and its end-effectors, though these systems can also still use telemanipulators for their input. One advantage of using the computerized method is that the surgeon does not have to be present, but can be anywhere in the world, leading to the possibility for remote surgery. One drawback relates to the lack of tactile feedback to the surgeon. Another drawback relates to visualization of the surgical site. Because the surgeon may be remote or the surgery may be percutaneous, is it difficult for the surgeon view the surgery as precisely as may be needed.

In the case of enhanced open surgery, autonomous instruments (in familiar configurations) replace traditional steel tools, performing certain actions (such as rib spreading) with much smoother, feedback-controlled motions than could be achieved by a human hand. The main object of such smart instruments is to reduce or eliminate the tissue trauma traditionally associated with open surgery. This approach seeks to improve open surgeries, particularly orthopedic, that have so far not benefited from robotic techniques by providing a tool that can discriminate between soft tissue and hard or non-fibrous tissue for removal or modification.

There exists, therefore, a need for a robotic system that can be used by a surgeon to easily and safely remove or modify bone, cartilage and disk material for orthopedic procedures, particularly but not limited to the spine. The robotic surgical system should provide ultrasound capabilities to provide the surgeon with the capability of visualization and/or real time visualization of the surgical field.

BACKGROUND

The prior art has provided rotary bone, cartilage, and disk removal tool assemblies. A problem with rotary bone, cartilage, and disk removal tool assemblies is caused by an encounter with fibrous material, which may wrap about a rotary cutting tool and cause unwanted damage. The prior art has also provided rotary oscillating bone, cartilage, and disk removal tool assemblies. However, due to the high risk of damage to a patient, surgical procedures that are assisted or completed through the use of multi-axis robots in combination with rotary bone or non-fibrous tissue removal tools have remained unused.

SUMMARY OF THE INVENTION

The present invention provides an apparatus, system and method for providing robotically assisted surgery that involves the removal of bone or non-fibrous type tissues during a surgical procedure. The system utilizes a multi-axis robot having a reciprocating tool that is constructed and arranged to remove hard or non-fibrous tissues while leaving soft tissues unharmed. The multi-axis robot may be controlled via computer or telemanipulator, which allows the surgeon to complete a surgery from an area adjacent to the patient to thousands of miles away. The system also provides ultrasound, also referred to as sonography, to develop real time images of the surgical field to assist the surgeon in successfully completing the surgery.

Accordingly, it is an objective of the present invention to provide an oscillating tool that can be used in combination with a multi-axis robot to remove bone.

It is another objective of the present invention to provide an oscillating tool that can be used in combination with a multi-axis robot to remove non-fibrous tissue.

It is a further objective of the present invention to provide an oscillating tool that can be removably secured to the distal arm of a multi-axis robot to allow the oscillating tool to be interchanged with other tools.

It is yet another objective of the present invention to provide an oscillating tool that can be utilized on robots having various constructions.

It is a still further objective of the present invention to provide an oscillating tool that utilizes a removable and replaceable cutter.

Yet another objective of the present invention is to provide a robotic surgical system that utilizes ultrasound to provide real time images to the surgeon completing or controlling the robotic surgery.

Still yet another objective of the present invention is to provide a robotic surgical system wherein the robot includes an automatic tool changer, allowing the surgeon to quickly interchange tools on the robotic arm.

A further objective of the present invention is to provide a robotic surgical system that utilizes two robotic arms functioning in tandem so that one robotic arm provides ultrasonic images to allow the second robotic arm to complete the desired surgical procedure.

Other objects and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE FIGURES

FIG. 23 is a side view of one embodiment of the present system utilizing two robotic arms.

DETAILED DESCRIPTION OF THE INVENTION

Figure 1:
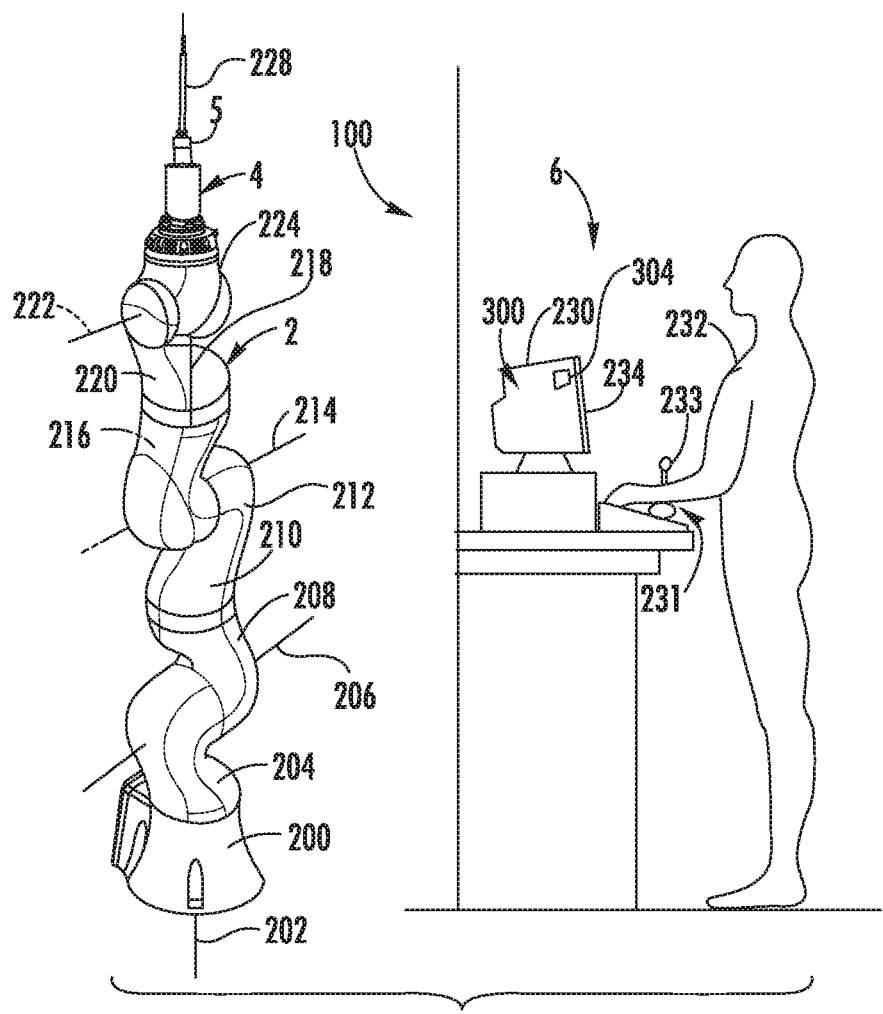
FIG. 1 illustrates one embodiment of the multi-axis robot along with an operator station.
Figure 2:
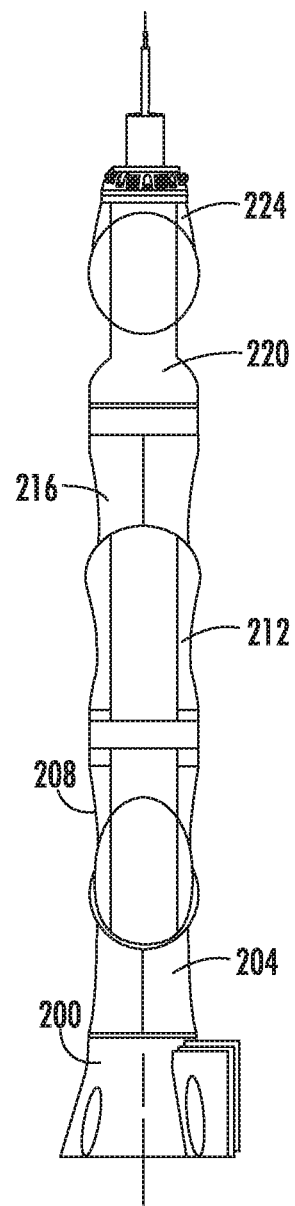
FIG. 2 illustrates a side view of one embodiment of the multi-axis robot.
Figure 3:
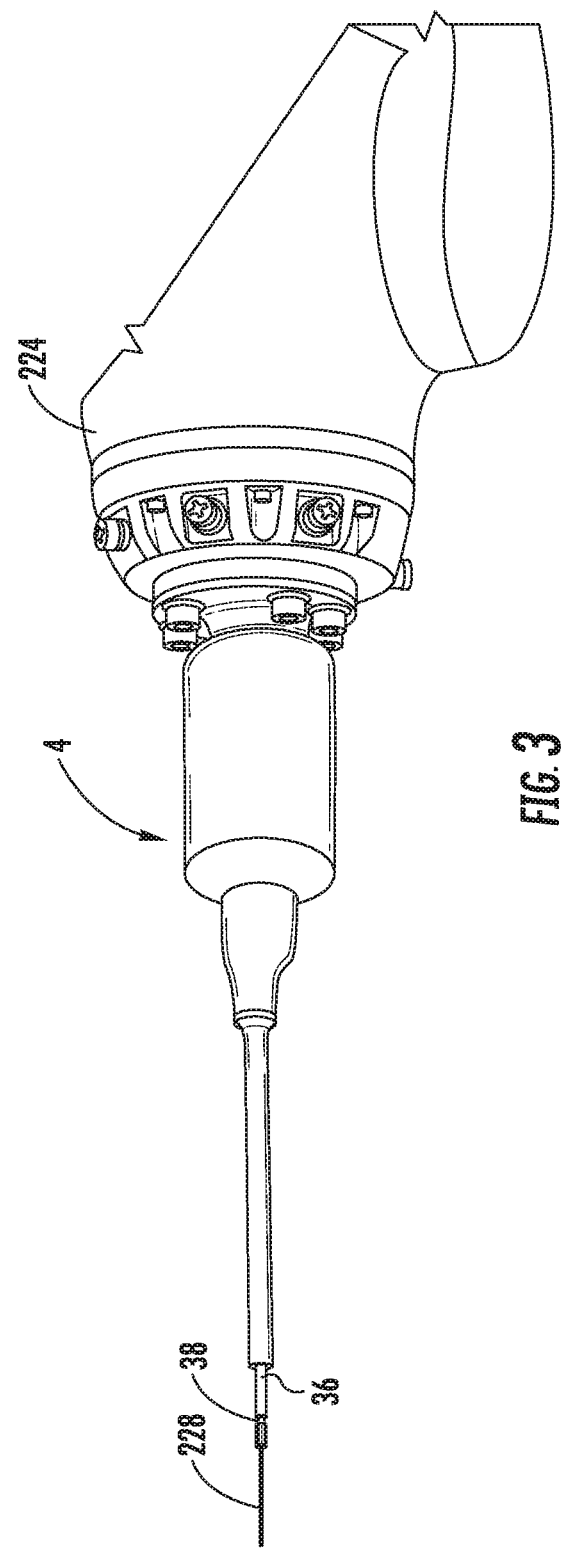
FIG. 3 illustrates an isometric view of one embodiment of the oscillating tool secured to the distal arm of a multi-axis robot.
Figure 4:
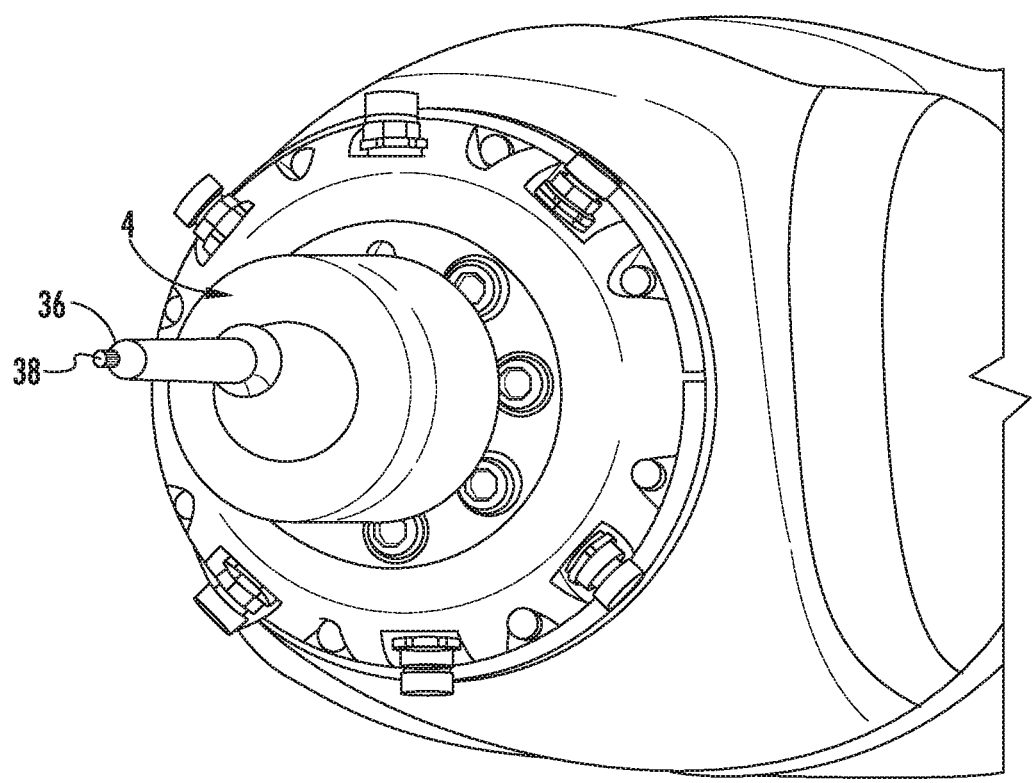
FIG. 4 is an isometric end view of the embodiment illustrated in FIG. 3.
Figure 5:
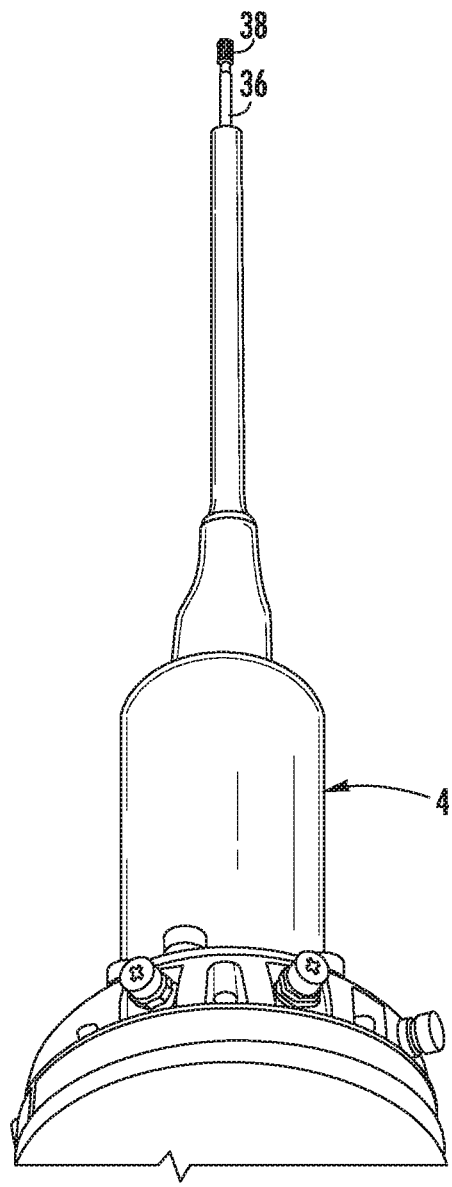
FIG. 5 is a side isometric view of the embodiment illustrated in FIG. 3.
Figure 6:
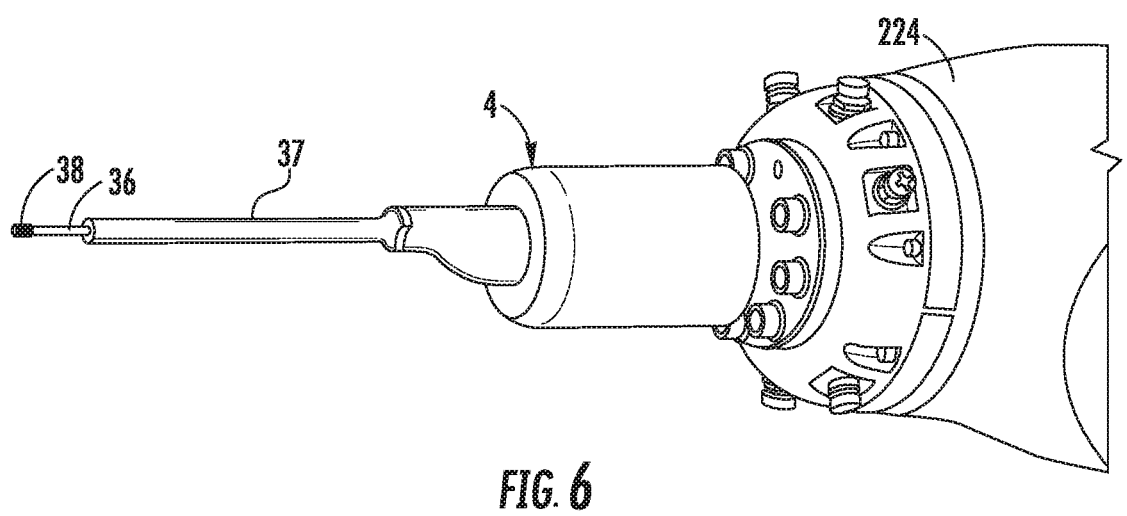
FIG. 6 is a front isometric view of the embodiment illustrated in FIG. 3.
Figure 7:
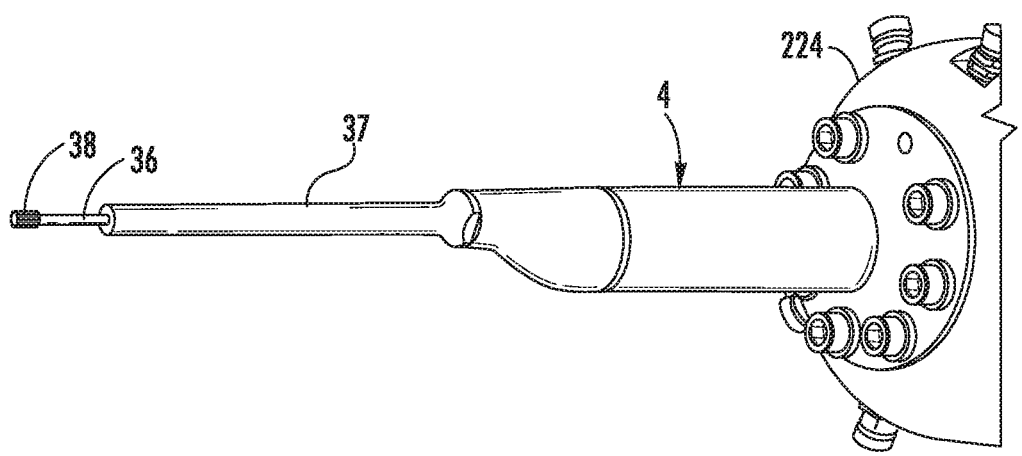
FIG. 7 is an isometric view of an alternative embodiment of the oscillating tool secured to the distal arm of the multi-axis robot.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Referring to FIGS. 1-23, a robotic surgical system 100 is illustrated. The robotic surgical system 100 generally includes a multi-axis robot 2, a tool 4 (oscillating tool assembly below) with an effector 5 on a distal end thereof, and an operator station 6. The tool 4 is preferably an oscillating tool as more fully described below. The multi-axis robot 2 includes a plurality of axes about which the oscillating tool 4 can be precisely maneuvered and oriented for surgical procedures. In a preferred, but non-limiting, embodiment, the multi-axis robot includes seven axes of movement. The axes of movement include the base axis 202 generally centered within the base 200 and about which the first arm 204 rotates. The second axis 206 is substantially perpendicular to the first axis 202 and about which the second arm 208 rotates. The second arm 208 includes the third axis 210 about which the third arm 212 rotates. The third arm 212 includes the fourth axis of rotation 214 which is oriented substantially perpendicular with respect to the first axis 202 and substantially parallel to the second axis 206. The fourth arm 216 rotates about the fourth axis 214. The fourth arm 216 includes the fifth axis 218 about which the fifth arm 220 rotates. The fifth arm 220 includes the sixth axis 222 which includes the most available rotation about the sixth axis 222 for the wrist 224 of the robot. The wrist 224 carries the tool 4 and effector 5 and has a seventh axis of rotation 228 for the cutting tool. The wrist 224 is at the distal end of the fifth arm 220. It should be noted that each axis of rotation provides an additional freedom of movement for manipulation and orientation of the tool 4. It should also be noted that while the multi-axis robot 2 is only illustrated with the tool 4, the preferred embodiment is capable of changing the effector to a variety of tools that are required to complete a particular surgery. Drives, not shown, are utilized to move the arms into their desired positions. The drives may be electric, hydraulic or pneumatic without departing from the scope of the invention. Rotational position can be signaled to a computer 230, as with an encoder (not shown) associated with each arm 206, 208, 212, 216, 220 and other components having an axis of rotation. In the preferred embodiment, the drives are in electrical communication with the computer 230, and may further be combined with a telemanipulator, or pendant (not shown). The computer 230 is programmed to control movement and operation of the robot(s) 2 through a controller portion 231, and can utilize a software package such as ExcelsiusGPS™ from Globus. Alternatively, other software programming may be provided without departing from the scope of the invention. The computer 230 can have a primary storage device (commonly referred to as memory) and/or a secondary storage device that can be used to store digital information such as images described herein. Primary and secondary storage are herein referred to as storage collectively, and can include one or both primary and secondary storage. The system 100 may further include sensors positioned along various places on the multi-axis robot 2, which provide tactile feedback to the operator or surgeon 232. The computer 230 is electrically connected or coupled to the multi-axis robot 2 in a manner that allows for operation of the multi-axis robot 2, ranging from positions adjacent the robot to thousands of miles away. The computer 230 is preferably capable of accepting, retaining and executing programmed movements of the multi-axis robot 2 in a precise manner. In this manner, skilled surgeons can provide surgical care in areas, such as battlefields, while the surgeon is safe from harm's way. The controller 231 can include a movement control input device 233, such as a joy stick, keyboard, mouse or electronic screen 306, see FIG. 19, that can be touch activated. The screen 306 can be part of the monitor 234. Tool change commands can be input using the screen 306.

Referring to FIGS. 3-12, various embodiments of the oscillating tool 4 being utilized as an effector are illustrated. The oscillating tool assembly 4 can be used in surgical operations, such as spinal surgery, wherein bone, cartilage, disk, and other non-fibrous body material may be removed, such as from the spine. The oscillating tool assembly 4 has an output spindle 36 which is driven to rotate in both directions, or rotary oscillate about its axis 228. The spindle 36 supports a cutting tool 38, which is driven by the spindle 36 to rotate partially in both directions with a limited range of rotation. Such oscillatory cutting is effective for bone, cartilage, and disk removal by a shearing operation, while effective in minimizing damage to any fibrous material. If the cutting tool 38 inadvertently contacts fibrous material, such as a nerve, during the cutting operation, the fibrous material is likely to be oscillated due to the flexibility of the fibrous material with minimal shearing, thereby minimizing damage to the fibrous material.

Figure 10:
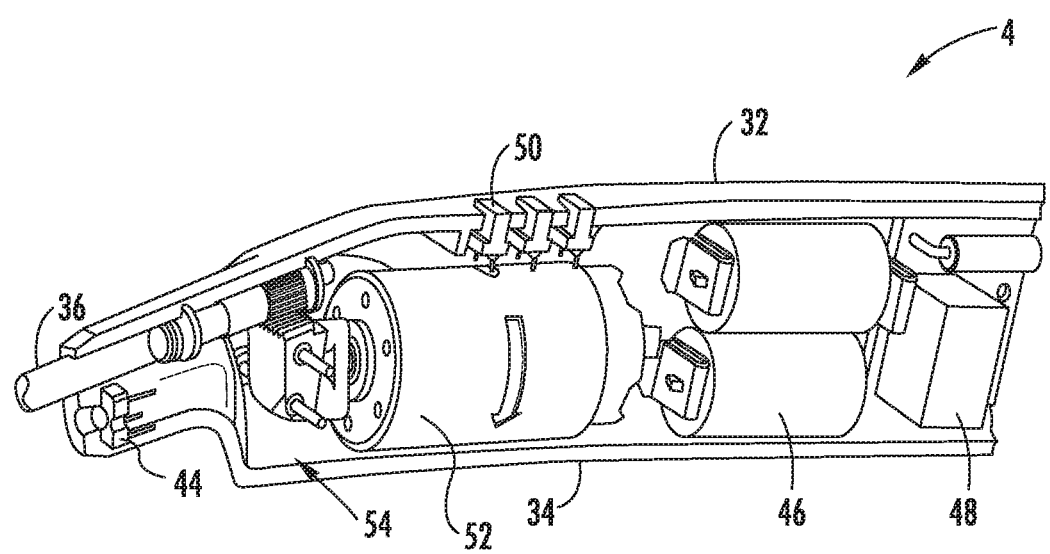
FIG. 10 is a partial section view illustrating one embodiment of the oscillating tool.

FIG. 10 illustrates some internal components of the oscillating tool assembly 4. A power source may be provided by a battery supply 46 oriented in the housing 32. The battery supply 46 may be charged or recharged by the multi-axis robot 2. Electronics 48 are provided in the housing 32 for controlling the operations of the tool assembly 4. The power switch (not shown) may be remotely operated via the computer 230, telemanipulator, or pendant. A plurality of indicator lamps 50 may be provided on the housing 32 and illuminated by LEDs for indicating operational characteristics of the tool assembly 4, such as the state of charge of the battery supply 46. Alternatively, the tool 4 may communicate wirelessly via Bluetooth, ZIGBY chip or the like to the computer 230, whereby the signal is visible on the monitor 234 either locally and/or remotely.

Figure 11:
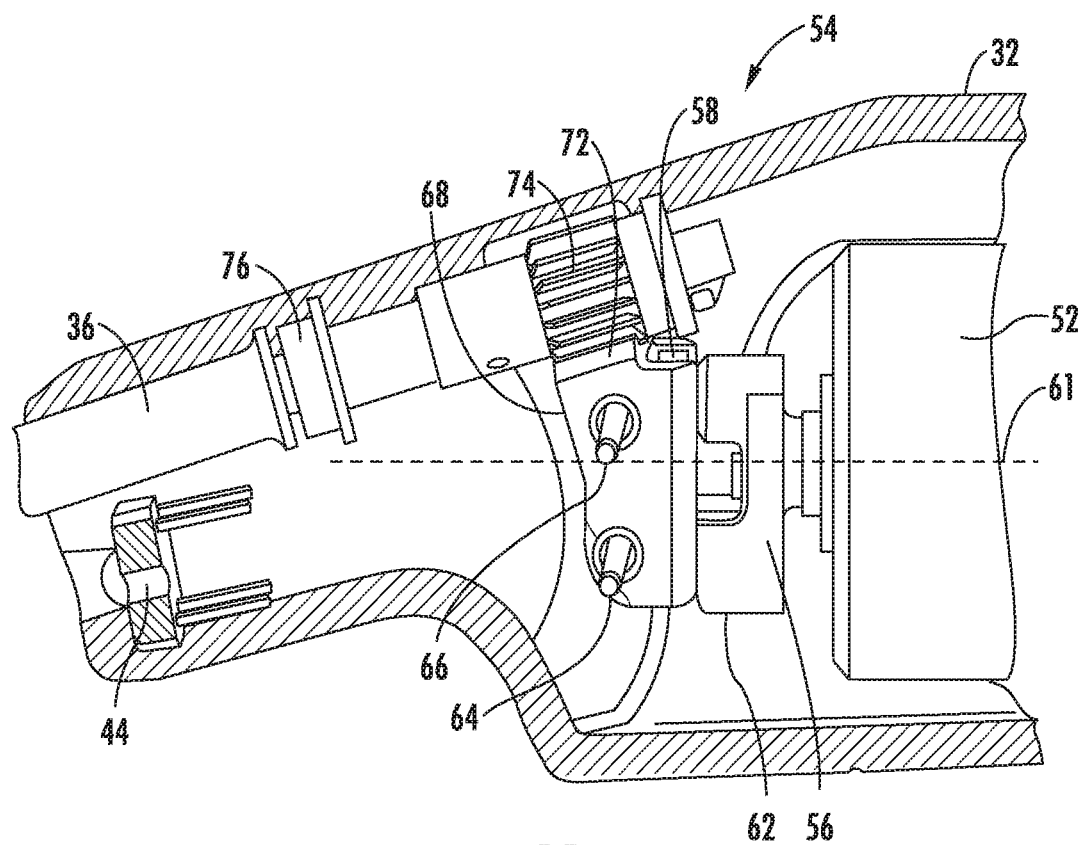
FIG. 11 is a partial section view of the embodiment illustrated in FIG. 10.
Figure 12:
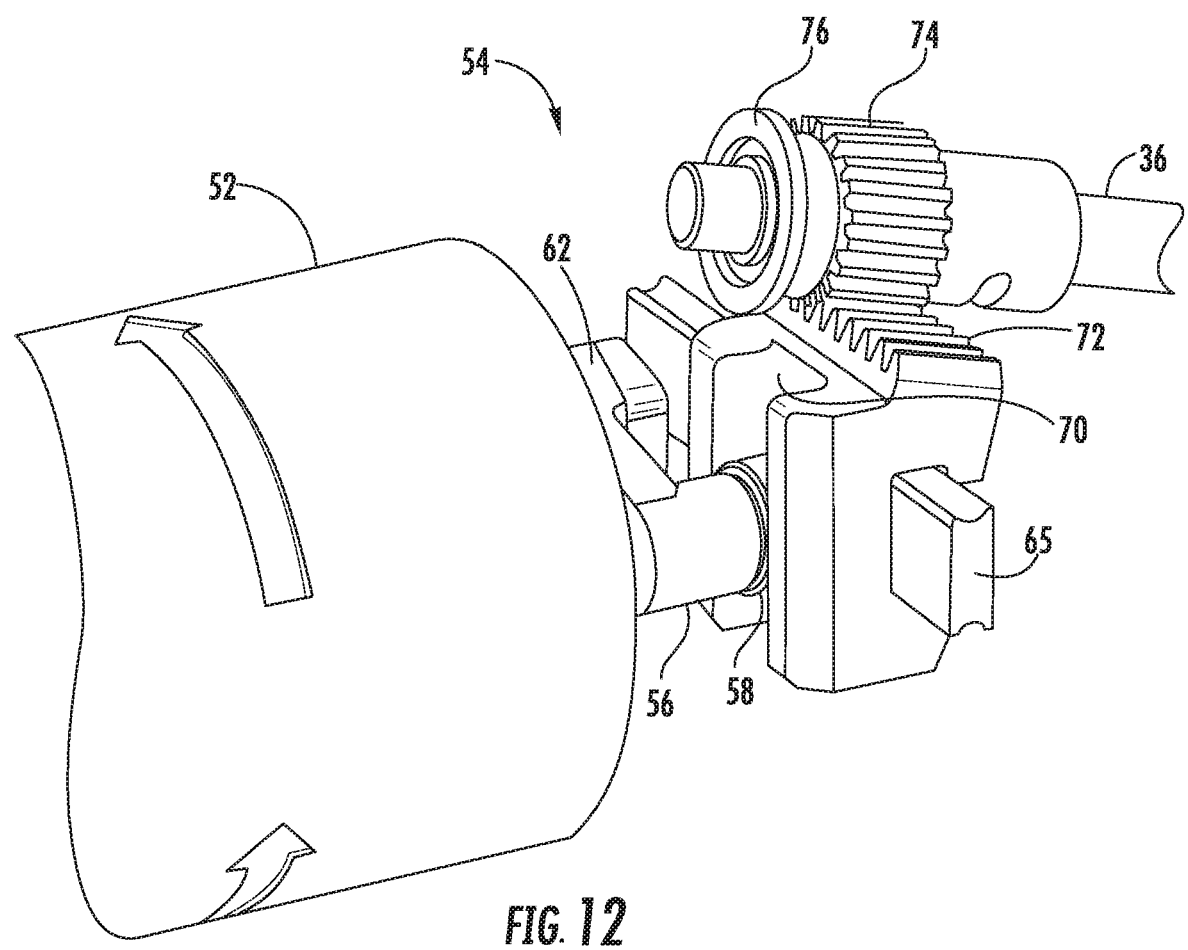
FIG. 12 is a partial isometric view of the embodiment illustrated in FIG. 10 illustrating a scotch yoke mechanism for creating oscillatory movement.

A motor 52 is mounted in the housing 32 for providing a rotary input. The motor 52 is powered by the battery supply 46 when controlled by the electronics 48. The motor 52 drives a transmission 54 for converting continuous rotary motion from the motor 52 to rotary oscillation to the spindle 36. The spindle 36 is journalled in the housing 32 and driven by the transmission 54. The spindle 36 is preferably straight, but may be angled relative to the housing 32 as depicted in FIGS. 10-12 for specific operations. Cooling fins, or a cooling fan (not shown), may be attached to or near the motor 52 for cooling the motor 52 and/or the tool assembly 4.

Referring now to FIGS. 11-12, the motor 52 drives an eccentric drive 56. The eccentric drive 56 includes a roller 58 supported to rotate upon the drive 56, which is offset from an axis 60 of the motor 52. Thus, rotation of the eccentric drive 56 causes the roller 58 to revolve about the axis 60. The eccentric drive 56 also includes a counter-balance 62 offset from the axis 60, opposed from the roller 58, to counter-balance the transmission 54 and to minimize unwanted vibrations. The counter-balance 62 can be formed integrally with the eccentric drive 56 according to at least one embodiment. The counter-balance 62 may include an additional weight according to another embodiment. Alternatively, the roller 58 may be a pin. A guide, illustrated herein as a pair of pins 64, 65 are supported in the housing 32, generally perpendicular to the motor axis 61. Alternatively, a single rail (not shown) may be utilized without departing from the scope of the invention. A shuttle 68 is provided on the guide 64 for reciprocating translation upon the guide 64. The shuttle 68 includes a channel 70 that is generally perpendicular to the guide 64. The channel 70 receives the roller 58 of the eccentric drive 56. The channel 70 cooperates as a follower for permitting the roller 58 to translate along a length of the channel 70 while driving the shuttle 68 along the guide 64. The guide 64 may utilize bearings and/or rollers or the like to reduce friction.

Referring again to FIGS. 10-12, a gear rack 72 is formed upon the shuttle 68. The gear rack 72 is formed generally parallel to the spindle 36. A pinion gear or burr gear 74 is mounted to the spindle 36 in engagement with the gear rack 72, thereby providing a rack-and-pinion mechanism for converting the reciprocating translation of the shuttle 68 to rotary oscillation of the spindle 36. A pair of bearing assemblies 76 may also be provided in the housing for providing bearing support to the spindle 36. The transmission 54 may include any additional gearsets, as is known in the art, to vary speed or torque. According to one embodiment, a spur gear may be added to a motor output shaft to multiply speed of the roller 58.#

The eccentric drive 56 and shuttle 68 cooperate as a Scotch-yoke mechanism for converting continuous rotary motion to linear reciprocating motion. Although the Scotch-yoke mechanism is illustrated, any mechanism for converting rotary motion to reciprocation can be employed, such as a crank-and-slider mechanism, or the like. It should also be noted that, in some embodiments, the spindle 36 and spindle tube 37 (FIGS. 6, 7) are removable and replaceable from the remainder of the housing. In this manner, cutters or gear ratios that provide more or less oscillation can be easily changed to suit a particular need.

Figure 8:
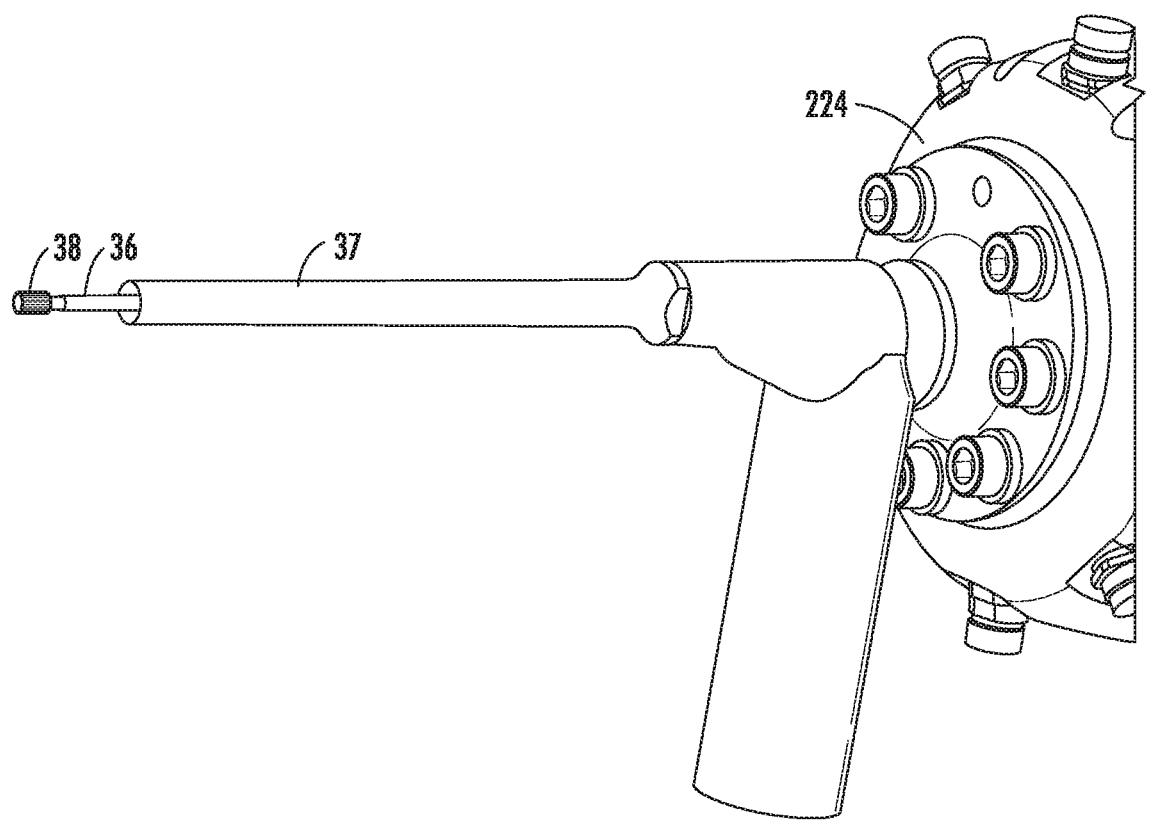
FIG. 8 is a front isometric view of an alternative embodiment of the oscillating tool secured to the distal arm of the multi-axis robot.
Figure 9:
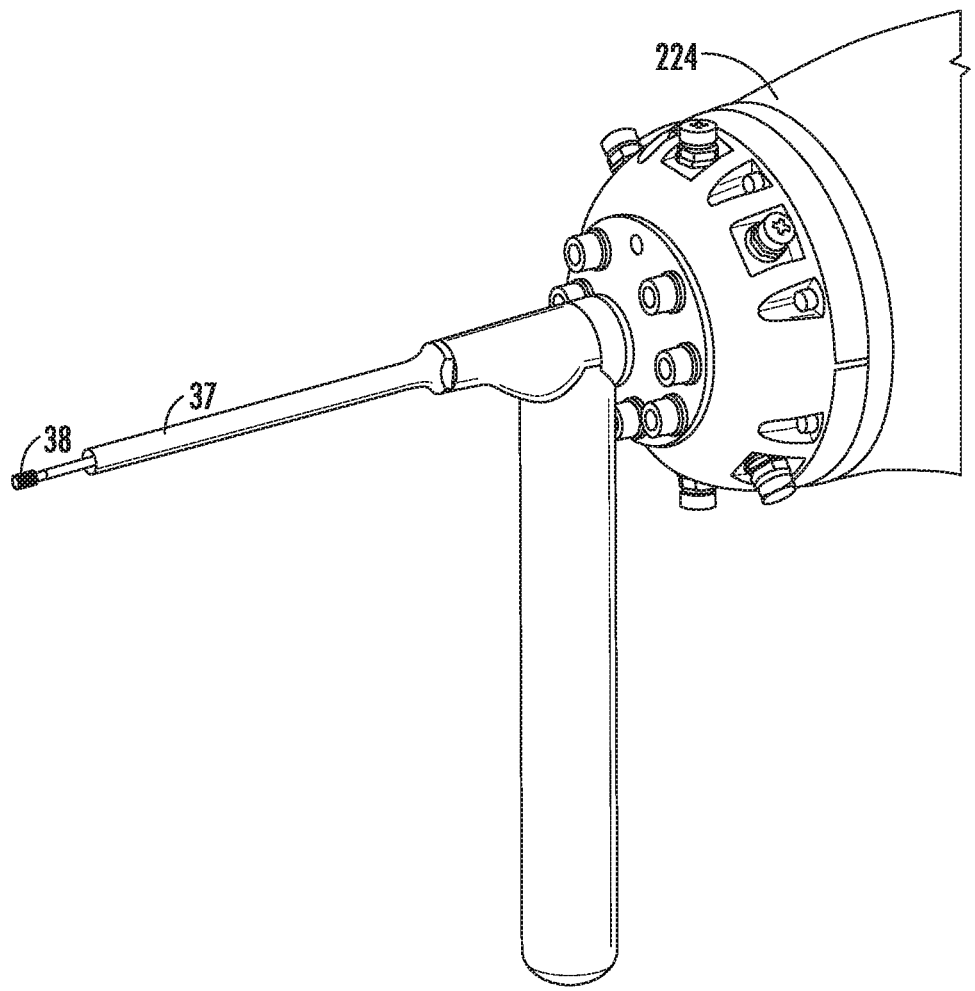
FIG. 9 is a front isometric view of an alternative embodiment of the oscillating tool secured to the distal arm of the multi-axis robot.

Referring to FIGS. 8 and 9, alternative embodiments of the oscillating tool assembly 4 are illustrated. In these embodiments, the electric motor 52 and transmission assembly 54 are oriented at about a right angle with respect to the spindle 36. This construction may provide advantages for types of operations by shortening the distance from the end of the wrist 224 to the end of the spindle 36.

Figure 13:
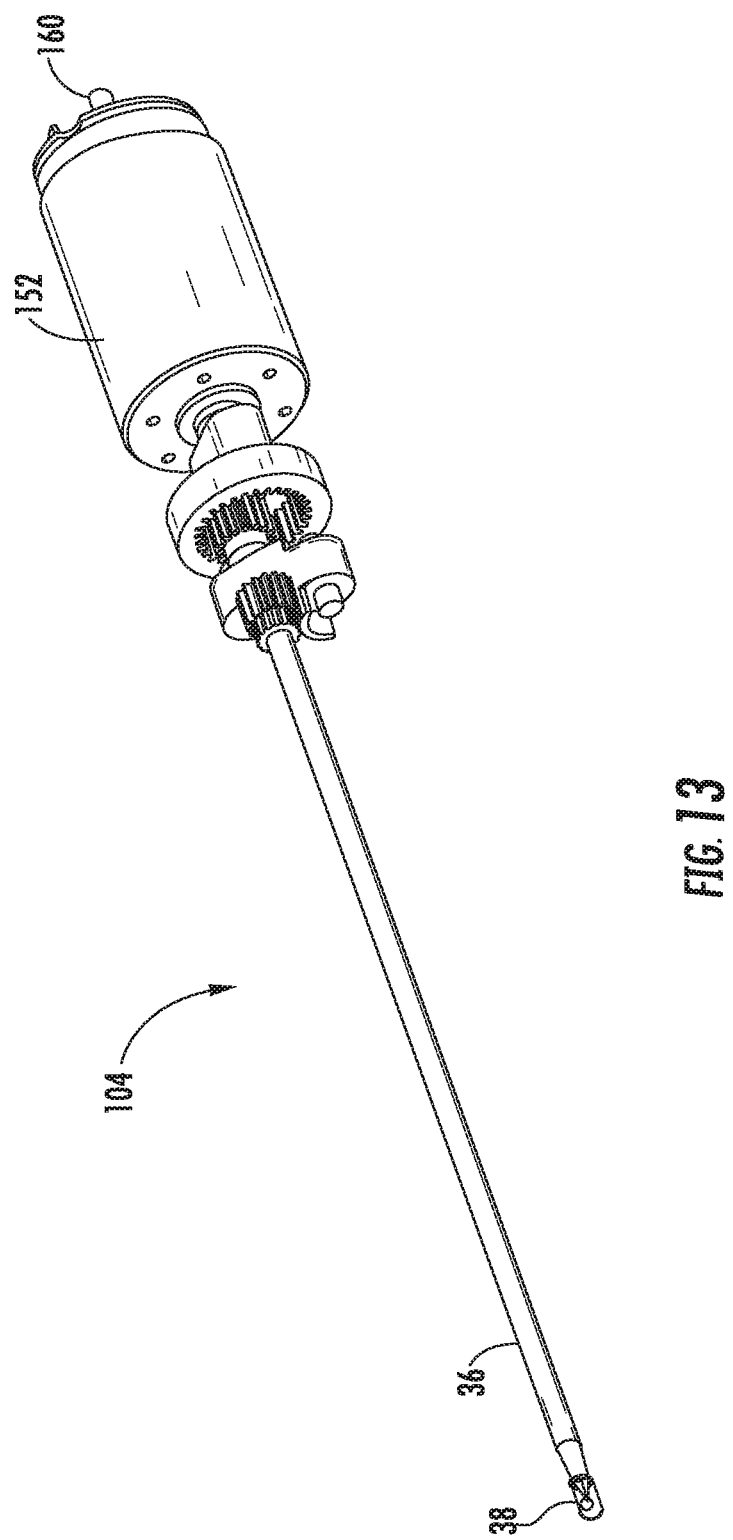
FIG. 13 is an isometric view of an alternative oscillating mechanism illustrated without the outer case.
Figure 14:
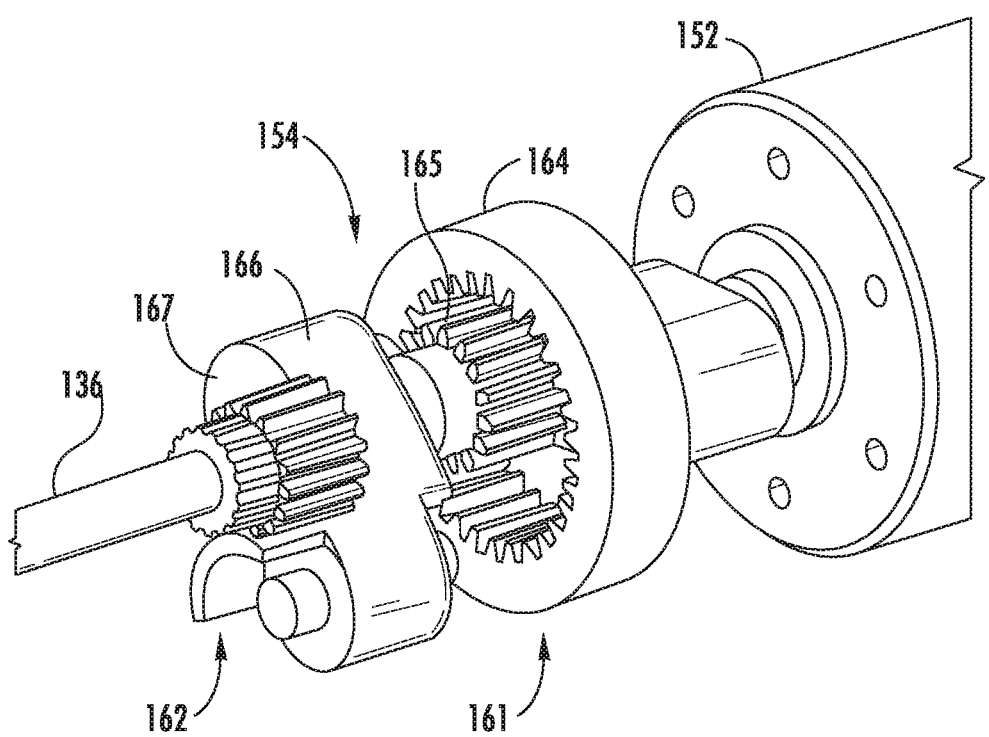
FIG. 14 is a partial isometric view of the embodiment illustrated in FIG. 13.
Figure 15:
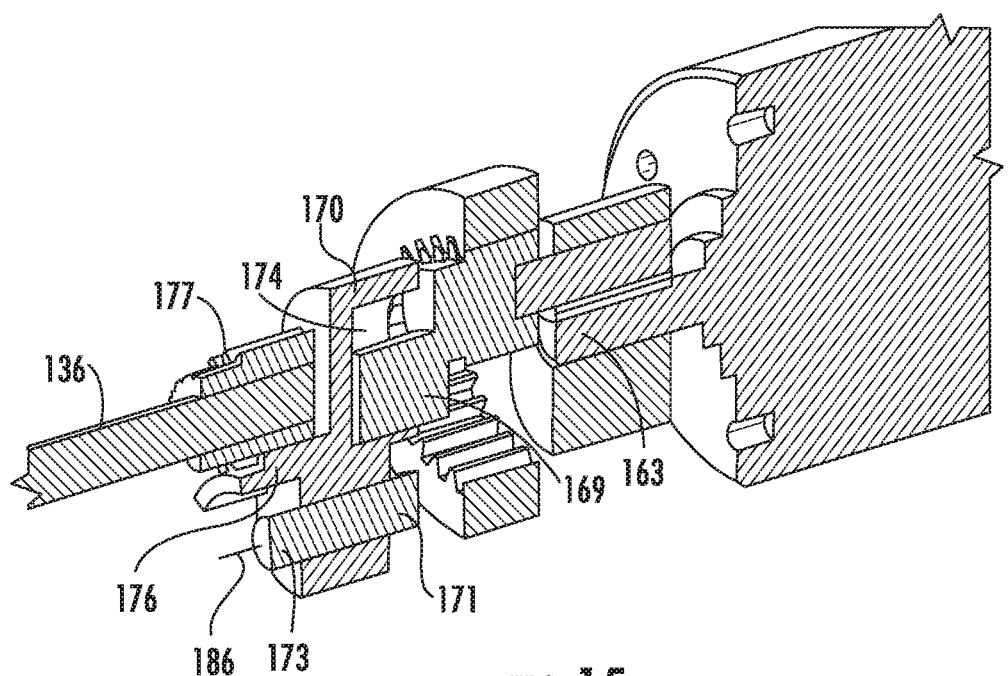
FIG. 15 is a partial isometric section view of the embodiment illustrated in FIG. 13.

Referring to FIGS. 13-15, an alternative embodiment of the oscillating tool 104, having the housing omitted for clarity is illustrated. The transmission 154 is positioned in the housing 132 and operably couples the shaft 136 to the motor 152, and is operable to convert the continuous rotary motion of the motor shaft 163 (FIG. 15) of the motor 152 to oscillating rotary motion of the shaft 136. By oscillating rotary motion, it is meant that the shaft 136 will rotate a portion of a complete revolution first in one rotation direction then in another rotation direction; say first counterclockwise, then clockwise, then counterclockwise again and so on. To effect this movement, the transmission 154 comprises two sections. The first section is designated generally 161, and is operable to convert the rotary motion of the shaft 163 of the motor 152 to reciprocating linear motion of a portion thereof, and the second section is designated generally 162, and is operable to convert that reciprocating motion to oscillating rotary motion.

In the illustrated embodiment, the transmission section 154 is in the form of a Cardan mechanism that utilizes an internal ring gear 164 and an external pinion gear 165, with the pinion gear 165 being positioned inside of and having its external gear teeth in engagement with the internal gear teeth of the ring gear 164. The gear ratio of the ring gear 164 to pinion gear 165 is 2:1. The ring gear 164 is suitably fixed in the housing 32 to prevent its motion relative to the housing 32. The pinion gear 165 is suitably mounted to a crank arm 166, which in turn is secured to the shaft 163 of the motor 152 and is offset from the axis of rotation of the shaft 163, whereby the pinion gear 165 revolves about the axis of rotation of the shaft 163 while inside the ring gear 164. Preferably, the crank arm 166 has a counterweight 167 opposite of where the pinion gear 165 is mounted to the crank arm 166. In a Cardan mechanism, one point on the pinion gear will move linearly in a reciprocating manner within the ring gear associated therewith. In the illustrated embodiment, the path of movement of this point is timed to move in a generally transverse plane relative to a portion of the transmission 154. Secured to the pinion gear 165, preferably in an integral manner, is a driver arm 169 that extends forwardly of the ring gear 164 for receipt in a follower 170 to effect movement of the follower 170 in response to movement of the driver arm 169. The follower 170 is suitably mounted in the housing 32 in a manner to permit its pivoting movement about an axle 171. The transverse linear movement of a spot on the pinion gear 165 is generally transverse to the longitudinal axis of elongate slot 174 in the follower 170. The axle 171 is suitably mounted in bearing supports 173 that are in turn suitably mounted to the housing 32. While only one bearing support 173 is shown, it is preferred that each end of the axle 171 have a bearing 173 associated therewith. It is to be understood that the axle 171 could utilize the follower 170 as a bearing for rotation of the follower 170 about the axle 171, and have the axle 171 mounted to the housing 32 in a fixed manner. The driver arm 169 is received within the elongate slot 174 for effecting movement of the follower 170 in a rotary oscillating manner. The follower 170 moves in an oscillating rotary manner about the axis 186 of the axle 171. When a portion of the driver arm 169 is moving in its linear path, portions of the arm 169 engage sides of the slot 174 to effect movement of the follower 170 in response to movement of the driver arm 169. In the illustrated structure, the driver arm 169 is offset to the outside diameter of the pinion gear 165, and thus its central axis does not move in a linear path, but will move in a series of arcs that are elongated in a horizontal plane and reduced in the vertical direction. This back-and-forth and up-and-down movement is accommodated by constructing the slot 174 to be elongated, as best seen in FIG. 15. As the driver arm 169 moves in its path, it affects oscillating rotary motion of the follower 170 about the axle 171. Two counterclockwise and two clockwise oscillations of the cutter 38 are affected, and four oval paths are traversed for each revolution of the pinion gear 65 within the ring gear 164. The follower 170 is provided with a sector gear 176 that is operably coupled to a gear 177 secured to the shaft 136. As the follower 170 moves, the shaft 136 moves in response thereto by engagement between the gears 176 and 177. Because the follower 170 moves in a rotary oscillating manner, the shaft 136 also moves in a rotary oscillating manner. The components of the transmission sections 161, 162 are configured relative to one another such that, when the rotary oscillating movement changes direction at the shaft 136, the applied torque by the motor 152 would be high; while at the center of one oscillation, the applied torque by the motor 152 would be lower. This assists in providing a high starting torque for the cutter 38 to reverse rotation direction.

Figure 16:
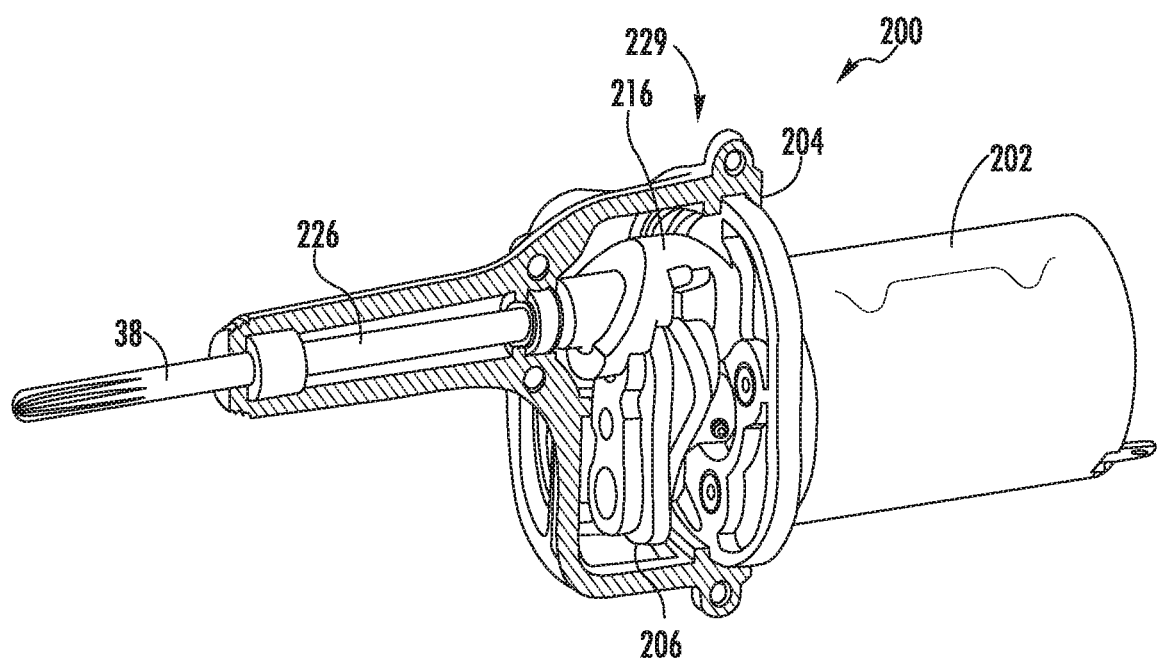
FIG. 16 is an isometric view of an alternative oscillating mechanism illustrated without the outer case.
Figure 18:
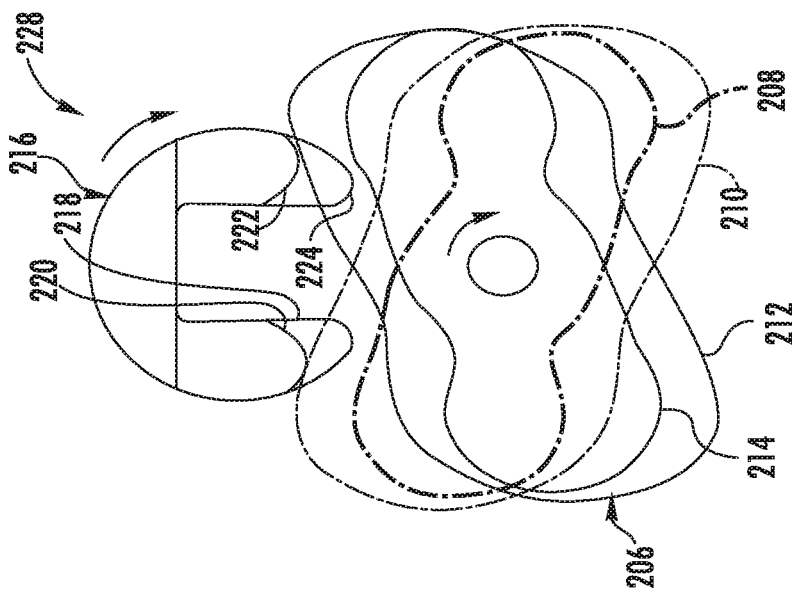
FIG. 18 is a partial section view illustrating a cam mechanism for creating the oscillating movement of the cutting tool.
Figure 17:
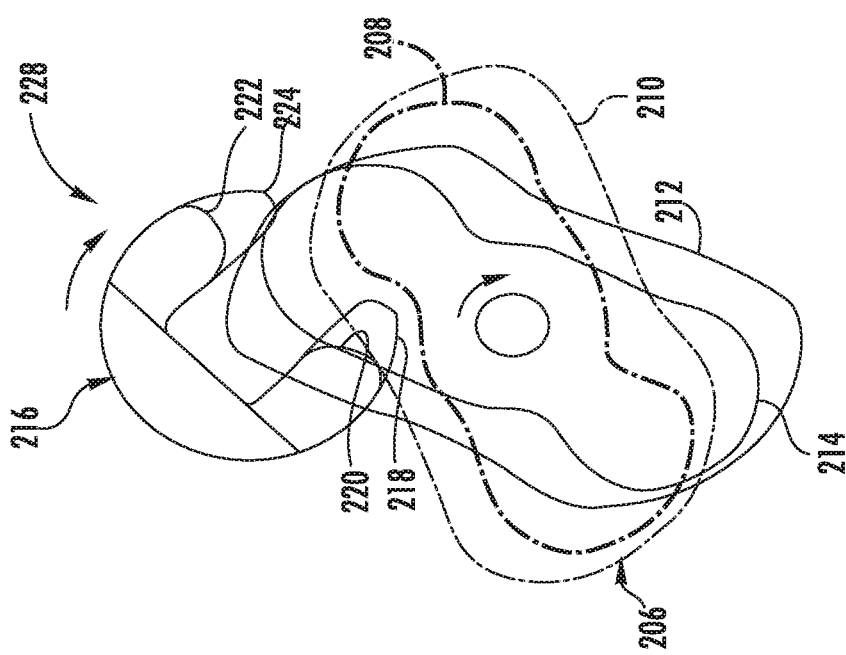
FIG. 17 is a partial section view illustrating a cam mechanism for creating the oscillating movement of the cutting tool.
Figure 19:
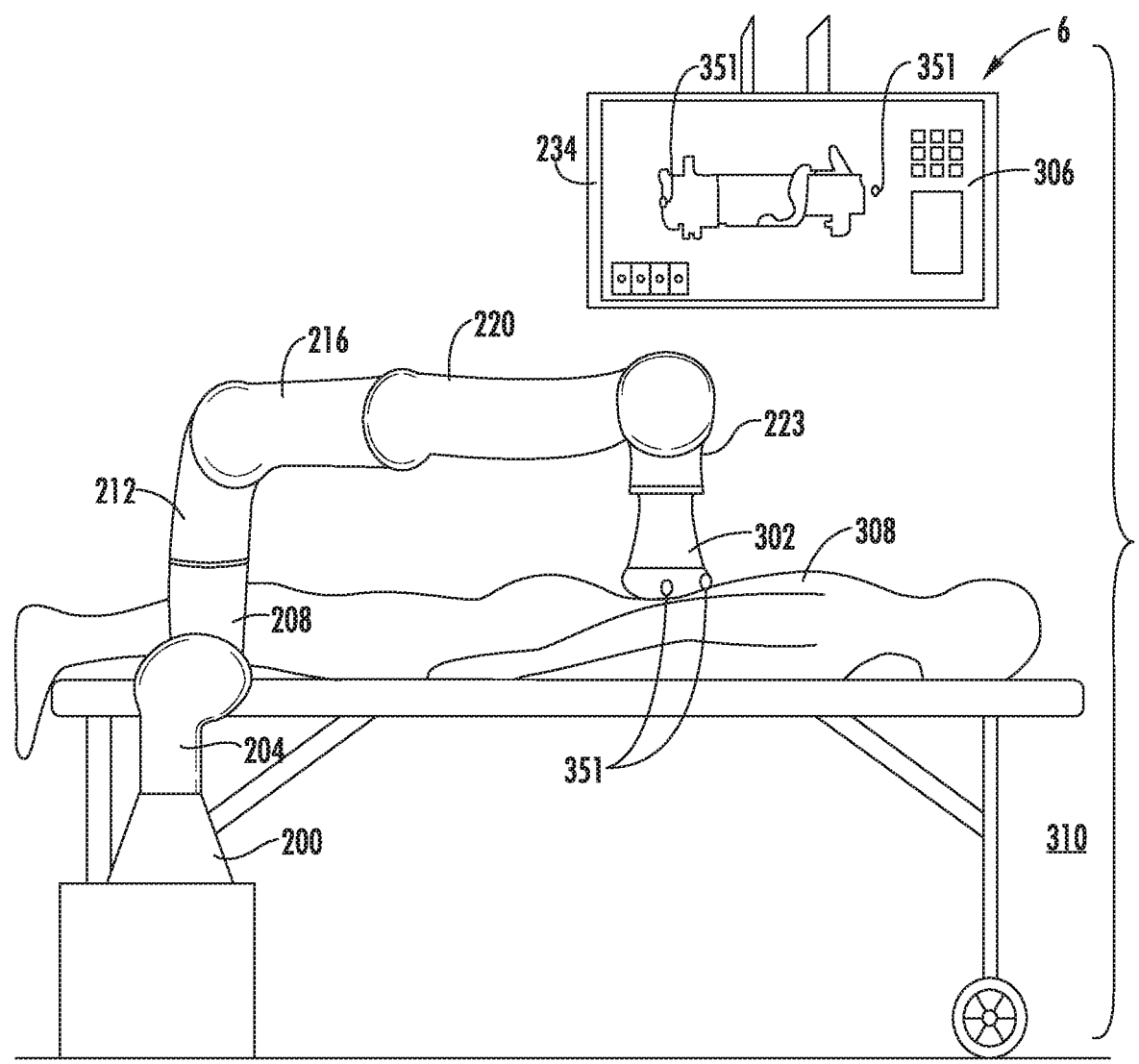
FIG. 19 is a side view illustrating a robotic arm with an ultrasound probe and a display of the image generated.

Referring to FIGS. 16-18, another alternative embodiment of the oscillating tool for use with the robotic surgical system 100 is illustrated. The alternative oscillating tool assembly 200 includes a motor 202 mounted in a housing 204. The motor 202 drives a cam mechanism 206 for continuous rotation. The cam mechanism 206 has four distinct cam profiles 208, 210, 212, 214 stacked axially from the motor 202. Each of the cam profiles 208, 210, 212, 214 is illustrated schematically in FIGS. 17-18. A follower mechanism 216 is mounted for rotation in the housing 204. The follower mechanism 216 has four follower profiles 218, 220, 222, 224, each for cooperating with one of the cam profiles 208, 210, 212, 214, as also illustrated in FIGS. 16-18. A spindle 226 is provided in the housing 204 with bearing support. The cam mechanism 206 and the follower mechanism 216 cooperate as a transmission 229 for converting one rotation of the cam mechanism into two rotary oscillations of the follower mechanism 216.

The electric motor 202 spins the cam mechanism 206 continually in one direction, which is clockwise in FIGS. 17-18. The cam profiles 208, 210, 212, 214 engage the follower profiles 218, 220, 222, 224 at two contact points at all times. At one contact point, the cam mechanism 206 pushes the follower mechanism 216 to rotate. At the other contact point, the cam mechanism 206 prevents the follower mechanism 216 from over-rotating. The profiles 208, 210, 212, 214 on the cam mechanism 206 work together to cause the follower mechanism 216 to rotationally oscillate in two directions. For the depicted embodiment, each of the four cam profiles 208, 210, 212, 214 consists of two symmetrical lobes, which causes the follower mechanism 216 to make two complete oscillations (back and forth twice) for every complete revolution of the motor 202. The cam mechanism 206 could also be designed asymmetrical, and/or so that it causes the follower mechanism 216 to make any number of oscillations, such as one, or more than two, per motor revolution.

In FIG. 17, the second cam profile 210 contacts the second follower profile 220 for preventing over-rotation of the follower mechanism 216, while the fourth cam profile 214 drives the fourth follower profile 224. In FIG. 18, the second cam profile 210 contacts the second follower profile 220 for driving the follower mechanism 216, while the third cam profile 212 engages the third follower profile 222 to prevent over-rotation of the follower mechanism. In FIG. 17, the first cam profile 208 contacts the first follower profile 218 for preventing over-rotation of the follower mechanism, while the third cam profile 212 drives the third follower profile 222, thereby reversing directions. In FIG. 18, the first cam profile 208 contacts the first follower profile to prevent over-rotation of the follower mechanism 216, while the fourth cam profile 214 drives the fourth follower profile 224. The process is repeated at FIG. 17.

Referring to FIGS. 1 and 19-23, an alternative embodiment is illustrated. In this embodiment, the robotic surgical system 100 generally includes one or two multi-axis robot(s) 2, an ultrasound imaging system 300, an effector such as an oscillating tool 4, and an operator station 6. Typically, a surgeon would utilize fluoroscopy or fluoroscopy in combination with computer tomography (CT) scans or the like in order to perform surgery on the spine or other skeletal parts. The CT scans are performed prior to the surgery so the surgeon can identify landmarks within the patient 308 and attempt to align the fluoroscopic image with the CT scan image to perform the surgery. However, the fluoroscopic images are often difficult to align because the patient is in a different position, causing distortion in the fluoroscopic imaging etc. Thus, in order to provide real time images to the surgeon 232, one of the robot(s) 2 may be fitted with an ultrasound imaging probe 302. The ultrasonic imaging probe 302 is electrically connected to an imaging system electronic controller 304 provided in the computer 230 which allows the operator to project the real-time images upon of monitor 234 and ensure proper overlay of the ultrasound image with the CT scan. The CT scan image(s) and ultrasonic image(s) can be stored in and recalled from the computer 230 storage and displayed on the monitor 234. The monitor 234 may be positioned in the operator station 6 and/or within the operating room 310. This construction allows the operator 232 to take fluoroscopic images without subjecting himself or herself to the radiation, while still allowing landmarks within the patient 308 to be closely identified and located for storage within the operator's station for use in the surgery. Thus, the operator can calibrate the robots positioning to correspond to the real-time ultrasonic image for completing the surgery. Afterwards, the operator can change the ultrasound probe 302 for a surgical instrument(s) tool 4 with effector 5 needed for the surgery in progressive order so that the tool(s) can be precisely maneuvered and oriented for surgical procedures. Springs or the like may also be utilized to control the amount of force that is used to push against the patient with the probe, e.g., the probe 302 can be spring loaded to reduce the risk of hard contact with a patient during probe movement.

Figure 20:
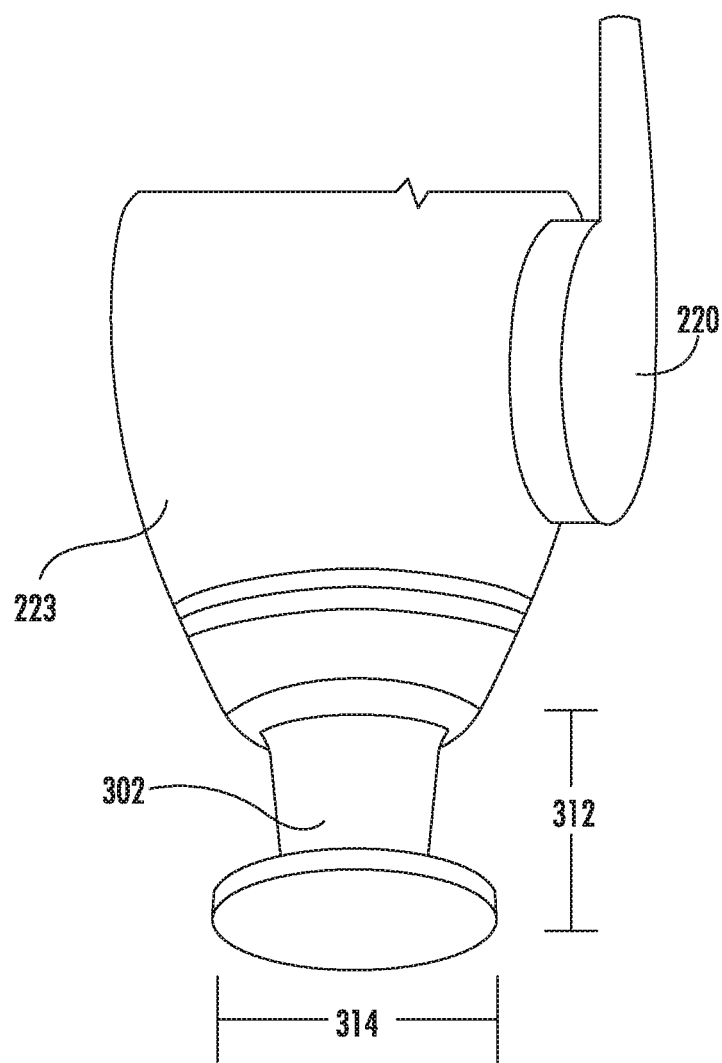
FIG. 20 is a partial view of the embodiment illustrated in FIG. 19.

Referring to FIG. 20, the wrist 223 portion of the robot carries the ultrasound probe 302. The ultrasound probe 302 is removably secured to the wrist 223 to allow probes or tools having different configurations to be interchanged by the robot upon command from the operator 232 through the computer 230 and coupled operator input controller 231 that allows the computer to know what the length 312 as well as the diameter 314 of the probe or tool 4 and effector 5 are. Thus, the robot can make fast approaches to the patient and slow down when the probe 302 or tool 4 is close to the patient, and still touch the patient in a soft controlled manner. In this manner, the computer 230 can also alter the three-dimensional positioning of the robot to correspond to the tool or probe size in relation to the real-time images.

Fiducial point devices 351 can be used to assist in determining the position of a tool 4 relative to a patient 308, and to assist in overlaying the various images, like the CT scan and ultrasound images. Typically for orthopedic surgery, fiducial point devices 351 are attached to a bone as with a screw. Such fiducial point devices are available from Northern Digital, Inc.

Figure 21:
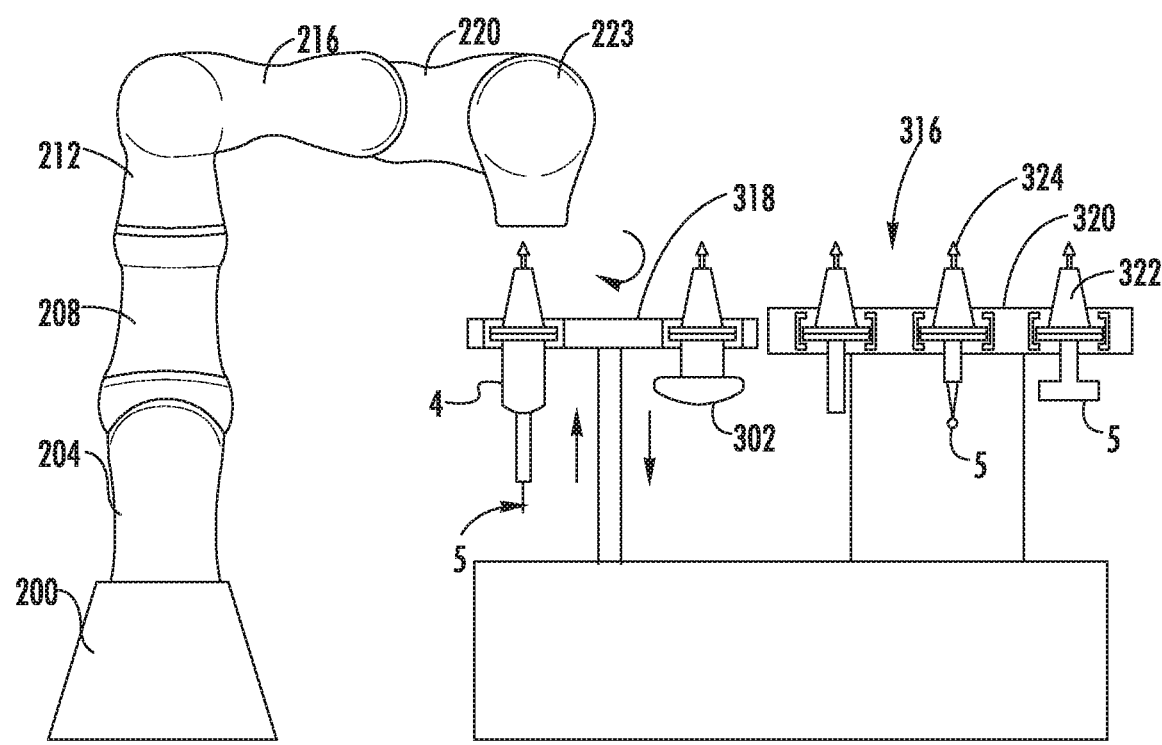
FIG. 21 is a side view illustrating one embodiment of a tool change system for use with a robotic arm.

FIG. 21 illustrates an embodiment of the present device that includes an automatic tool changer 316. The automatic tool changer 316 is constructed and arranged to allow the tool 4 with effector 5 to be changed by the robot 2 in response to a command from the computer 230, input preferably by the operator 232. In operation, the wrist 224 of robot 2 is positioned in a predetermined place. A tool arm 318 rises or rotates to engage the tool in the wrist 224 which is released. The tool arm 318 then lowers to remove the tool 4 and rotates to position an alternative tool under the wrist 224. The tool arm 318 rises to position the new tool within the wrist 224 where the wrist engages the tool 4. The tool arm 318 may then either retain the removed tool or place it onto a carrousel or conveyor 320, which may include any number of tools. Each tool 4 is provided with a tapered or otherwise shaped shank 322 which is shaped to cooperate with a cavity within the wrist 224 to provide repeatable positioning. In at least one embodiment, each tool is also provided with a tang 324 which cooperates with a drawbar or draw mechanism (not shown) within the wrist 224 to pull the tool into the wrist in a controlled and repeatable manner. A tool changer such as the MC-16R, QC-11 and QC-21 made by ATI can also be used instead of the drawbar type just described. As stated earlier, the length and diameter of each tool is retained within the computer 230 in the operator's station 6 so that positioning of the robot 2 arms is altered to correspond to each tool. In this manner, one tool can be utilized and quickly changed to the next needed tool while still utilizing the calibration and positioning provided from the ultrasound imaging. In at least one embodiment, the robot can be configured to rotate the wrist of the 223 of the robot to measure the moment of the tool as a second check that the proper tool is inserted into the wrist.

Figure 22:
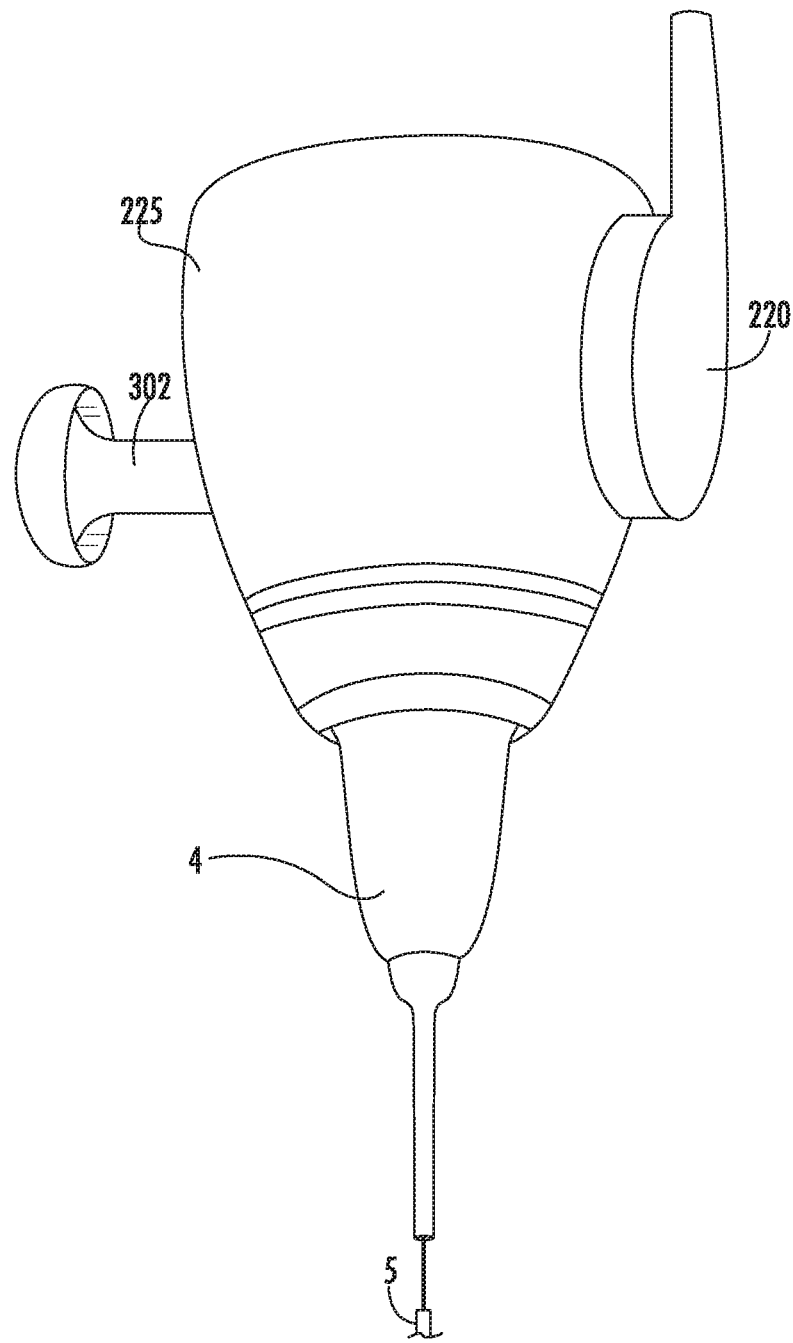
FIG. 22 is an isometric view of one embodiment of the robotic arm including an ultrasonic probe and an oscillating tool.

Referring to FIG. 22, an alternative embodiment is illustrated. In this embodiment, the ultrasound probe 302 is secured to a side or other surface of the wrist 223. This construction allows the wrist 223 to be simply rotated to touch the ultrasound imaging probe 302 onto the patient 308 to provide imaging and/or repositioning of the wrist 223 with respect to the image. Once the image and positioning are checked or rechecked, the wrist 223 can be rotated to use the tool also carried by the wrist. In this embodiment, the computer 230 keeps track of both the length 312 and diameter 314 of the ultrasound probe 302 and tool 4 so that precise locations are maintained when switching from the probe to the tool or between tools.

Referring to FIG. 23, an alternative embodiment is illustrated. In this embodiment, the system is provided with two or more robots 2 which work in unison and communicate positioning with the operator station 6 and each other to prevent collisions and coordinate actions. As illustrated, one robot 2 utilizes the ultrasound imaging probe 302, while the other robot utilizes the tool 4. In this manner, images can be taken simultaneously with operation of the cutting, drilling or other tools 4. This construction allows positioning corrections or other manipulations of the tools to be made as the surgery is occurring. It should be noted that the automatic tool changer may be used in conjunction with this or any other embodiment disclosed herein to add versatility to the system. It should also be noted that while the ultrasound tool is illustrated as having a different trajectory than that of the robot with the tool, the second robot will preferably direct the ultrasound on an intersecting trajectory with the cutting tool.

The present invention is better understood by a further description of its operation. A patient 308 is scheduled for surgery. In preparation, a first image of the surgical sight is created, for example, with a CT scan. Preferably, the first image is three-dimensional. The first image is digitally stored in the computer 230. At least one and preferably a plurality of fiducial point devices 351 are secured to the patient 308 and are included in the first image. The patient 308 is prepared for surgery and moved to the operating room 310. At least one robot 2 is located in the operating room, along with an automatic tool changer 316 positioned adjacent the robot(s) 2. The patient's surgical sight is exposed to the robot(s) 2. An ultrasound probe 302 is mounted to a robot 2, and a second digital image is created of the surgical sight and stored in the computer 230. The first and second images are overlaid by the computer 230 using the fiducial point device(s) 351 as a coordinating reference. At least the second image of the surgical sight in displayed on the screen 306 of the monitor 234, showing the surgical sight in real time at least at the beginning of surgery. Preferably, both the first and second images are simultaneously displayed on the monitor 234 and are both preferably three-dimensional images. If two robots 2 are used, a continuous second image can be displayed in real time or, if one robot 2 is used, the ultrasound probe can be used intermittently as selected by the operator 232 as, for example, between tool 4 changes. In a preferred embodiment, when an ultrasound probe is being operated during use of a tool 4, the ultrasound probe 302 is pointed in a direction to sense the effector 5 of the tool 4 and display it in the second image.

The computer 230, the operator controller 231, the monitor 234, screen 306, ultrasound probe 302 and robots 2 are operably coupled together to effect the various operations of each. While a single computer 230 is shown, it is to be understood that multiple computers can be in communication with one another to form a computer 230. For example, a remote computer can be coupled to a local computer through an internet server to form the computer 230. An operation control system includes the imaging control system 304, controller 231 and possibly screen 306, depending on its construction.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A robotic surgical system, the system comprising:
a first multi-axis robot having a plurality of interconnected arms, a first arm having a first end being mounted to a base for rotation about a first axis, a second end of said first arm rotationally connected to a first end of a second arm, said second arm being rotationally movable about a second axis relative to said first arm, said rotational movements completed in response to electrical signals received from a computer, a second end of said second arm having a tool holder positioned at a distal end thereof for retaining a surgical tool, said tool holder configured to retain or release said surgical tool in response to electrical signals sent from said computer, said computer electrically coupled to said first multi-axis robot and operable to control movement of said first arm, said second arm and said tool holder in response to commands sent as electrical signals from said computer, said computer storing a length and diameter of each surgical tool, so that positioning of the robot arms is altered to correspond to each surgical tool,
a monitor coupled to said computer and operable to configure said computer to display a path of movement of said surgical tool by providing electrical signals to said first multi-axis robot and receiving positional feedback of said first and said second arms, said monitor also operable to configure said computer to provide electrical signals to cause said multi-axis robot to move to a tool change position and display said tool change position for grasping and retaining said surgical tool in said tool holder.

2. The surgical system as set forth in claim 1, including a tool change rack positioned within the combined effective reach of said first arm and said second arm, said tool change rack being constructed and arranged to support a plurality of surgical tools in a predetermined arrangement, a positional location of each said surgical tool contained within said computer, whereby a said distal end of said interconnected first and second arms of said multi-axis robot can be maneuvered on command from said computer to a position above one of said plurality of surgical tools to be grasped by said tool changer holder secured to said distal end of said second arm.

3. The surgical system as set forth in claim 2, wherein said distal end of said interconnected arms of said multi-axis robot can be maneuvered on command from said computer to a position above a portion of said tool change rack, said computer sending a signal to said tool holder changer to drop said surgical tool out of said tool holder and into said tool change rack holder.

4. The surgical system as set forth in claim 1, wherein said computer is constructed and arranged to display a first image representing a portion of a patient, said computer also configured to receive and display a motion path of said distal end of said second arm of said multi-axis robot including said surgical tool with respect to said first image.

5. The surgical system as set forth in claim 4, wherein said surgical tool is an ultrasound probe, said robot receiving electrical signals from said computer to cause said distal end of said interconnected arms to move to a predetermined position, whereby said ultrasound probe sends a second image to said computer, said second image aligned and displayed over said first image.

6. The surgical system as set forth in claim 5, including a second multi-axis robot having a plurality of interconnected arms, a third arm having a first end being mounted to a base for rotation about a third axis, a second end of said third arm rotationally connected to a first end of a fourth arm, said fourth arm being rotationally movable about a second axis relative to said third arm, said rotational movements completed in response to electrical signals received from said computer, a second end of said fourth arm having a second tool holder positioned at a distal end thereof for retaining a surgical tool, said second tool holder configured to retain or release said surgical tool in response to electrical signals sent from said computer, said computer electrically coupled to said first multi-axis robot and said second multi-axis robot and operable to control movement of said first arm, said second arm, said third arm, said fourth arm, said tool holder and said second tool holder in response to commands sent as electrical signals from said computer.

7. The surgical system as set forth in claim 5, wherein said second image is displayed in real time.

8. The surgical system as set forth in claim 5, including at least one fiducial marker adapted to be secured to a portion of a patient anatomy, said fiducial marker constructed of a material that is visible in said first image and said second image, said fiducial marker utilized by said computer to align said first image and said second image for viewing.

9. The surgical system as set forth in claim 8, including a plurality of said fiducial markers.

10. The surgical system as set forth in claim 4, wherein said first image is a three dimensional image.

* * * * *